US012681024B2

(12) United States Patent
Taagaard et al.

(10) Patent No.: US 12,681,024 B2
(45) Date of Patent: Jul. 14, 2026

(54) DETERMINING INTERFERENCE CRITICALITY BASED ON ANALYTE AND CELL-FREE HEMOGLOBIN CONCENTRATIONS

(71) Applicant: Radiometer Medical ApS, Brønshøj (DK)

(72) Inventors: Michael Taagaard, Brønshøj (DK); Peter Frischauf, Brønshøj (DK)

(73) Assignee: Radiometer Medical ApS, Brønshøj (DK)

( * ) Notice: Subject to any disclaimer, the term of this patent is extended or adjusted under 35 U.S.C. 154(b) by 588 days.

(21) Appl. No.: 18/258,592

(22) PCT Filed: Dec. 20, 2021

(86) PCT No.: PCT/EP2021/086911
§ 371 (c)(1),
(2) Date: Jun. 21, 2023

(87) PCT Pub. No.: WO2022/136327
PCT Pub. Date: Jun. 30, 2022

(65) Prior Publication Data
US 2024/0044918 A1 Feb. 8, 2024

(30) Foreign Application Priority Data

Dec. 22, 2020 (EP) ..................................... 20216633

(51) Int. Cl.
*B01L 3/00* (2006.01)
*B01D 15/08* (2006.01)
(Continued)

(52) U.S. Cl.
CPC ..................................... *G01N 33/72* (2013.01)

(58) Field of Classification Search
CPC ....... G01N 33/57515; G01N 33/54387; G01N 33/57585; G01N 2470/04; G01N 33/92; G01N 33/54393
See application file for complete search history.

(56) References Cited

FOREIGN PATENT DOCUMENTS

| | | |
|---|---|---|
| JP | 2014-516944 A | 7/2014 |
| JP | 2018-533011 A | 11/2018 |

(Continued)

OTHER PUBLICATIONS

Jay, Dennis W., and D. Provasek. "Characterization and mathematical correction of hemolysis interference in selected Hitachi 717 assays." Clinical chemistry 39.9 (1993): 1804-1810. (Year: 1993).*

(Continued)

*Primary Examiner* — Jennifer Wecker
*Assistant Examiner* — Oyeleye Alexander Alabi
(74) *Attorney, Agent, or Firm* — FBT Gibbons LLP

(57) ABSTRACT

There is presented an apparatus (100) for automatically measuring an analyte concentration in a liquid sample (102) comprising the analyte and cell-free hemoglobin and for automatically determining a cell-free hemoglobin interference criticality, said apparatus comprising one or more sensors (104) for measuring the analyte concentration in the liquid sample, and a cell-free hemoglobin concentration in the liquid sample, and further comprising a data processing device (106) comprising a processor configured to determine the cell-free hemoglobin interference criticality based on the cell-free hemoglobin concentration, and the analyte concentration, and output a signal (108) indicative of the cell-free hemoglobin interference criticality at least in case the cell-free hemoglobin interference criticality is within a predetermined range.

24 Claims, 6 Drawing Sheets

(51) Int. Cl.

| | |
|---|---|
| *B01F 33/302* | (2022.01) |
| *B01F 33/3033* | (2022.01) |
| *B01J 8/00* | (2006.01) |
| *B01J 8/02* | (2006.01) |
| *B01J 20/285* | (2006.01) |
| *B01J 20/287* | (2006.01) |
| *B01J 20/32* | (2006.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C08L 5/08* | (2006.01) |
| *C12M 1/34* | (2006.01) |
| *C12M 3/06* | (2006.01) |
| *C12N 1/14* | (2026.01) |
| *C12N 1/20* | (2026.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/6851* | (2018.01) |
| *C12Q 1/686* | (2018.01) |
| *G01K 1/14* | (2021.01) |
| *G01N 1/44* | (2006.01) |
| *G01N 15/10* | (2024.01) |
| *G01N 15/14* | (2024.01) |
| *G01N 15/1433* | (2024.01) |
| *G01N 21/01* | (2006.01) |
| *G01N 21/03* | (2006.01) |
| *G01N 21/05* | (2006.01) |
| *G01N 21/29* | (2006.01) |
| *G01N 21/33* | (2006.01) |
| *G01N 21/35* | (2014.01) |
| *G01N 21/65* | (2006.01) |
| *G01N 21/75* | (2006.01) |
| *G01N 21/77* | (2006.01) |
| *G01N 27/07* | (2006.01) |
| *G01N 27/28* | (2006.01) |
| *G01N 27/416* | (2006.01) |
| *G01N 30/02* | (2006.01) |
| *G01N 30/60* | (2006.01) |
| *G01N 30/72* | (2006.01) |
| *G01N 31/10* | (2006.01) |
| *G01N 31/12* | (2006.01) |
| *G01N 33/543* | (2006.01) |
| *G01N 33/557* | (2006.01) |
| *G01N 33/564* | (2006.01) |
| *G01N 33/574* | (2006.01) |
| *G01N 33/575* | (2026.01) |
| *G01N 33/57515* | (2026.01) |
| *G01N 33/58* | (2006.01) |
| *G01N 33/68* | (2006.01) |
| *G01N 33/72* | (2006.01) |
| *G01N 35/00* | (2006.01) |
| *H05B 45/10* | (2020.01) |

(56) References Cited

FOREIGN PATENT DOCUMENTS

| | | | | |
|---|---|---|---|---|
| WO | WO-2017085180 A1 * | 5/2017 | ........ | B01L 3/502715 |
| WO | WO-2020033192 A1 * | 2/2020 | .......... | G01N 33/721 |

OTHER PUBLICATIONS

Dupuy, Anne Marie et al., "Determination of hemolysis cut-offs for biochemical and immunochemical analytes according to their value," Clinical Chemistry and Laboratory Medicine, vol. 58, No. 8, (2020).

Grieme, Caleb et al., "Impact of Endogenous and Exogenous Interferences on Clinical Chemistry Parameters Measured on Blood Gas Analyzers," Clinical Laboratory, vol. 63, No. 3, pp. 561-568 (2017).

Jay, D.W. et al., "Characterization and mathematical correction of hemolysis interference in selected Hitachi 717 assays", Clinical Chemistry, vol. 39, No. 9 (1993).

Lippi, Giuseppe et al, "Practical recommendations for managing hemolyzed samples in clinical chemistry testing," Clinical Chemistry and Laboratory Medicine, vol. 56, No. 5, pp. 718-727 (2018).

Prochazka, J. et al., "Haemolysis influence on the determination of total and direct bilirubin," Klinicka Biochemie a Metabolismus, vol. 21, No. 4, pp. 215-219 (2013).

International Search Report of International Application No. PCT/EP2021/086911, dated Feb. 4, 2022 (3 pages).

Written Opinion of the International Search Authority for International Application No. PCT/EP2021/086911 (5 pages).

JP Office Action for 2023-538715 mailed Apr. 26, 2024, pages.

* cited by examiner

DETERMINING INTERFERENCE CRITICALITY BASED ON ANALYTE AND CELL-FREE HEMOGLOBIN CONCENTRATIONS

This application is a national stage filing under 35 U.S.C. § 371 of International Application No. PCT/EP2021/086911, filed on Dec. 20, 2021, which claims priority to European Patent Application No. 20216633.6, filed on Dec. 22, 2020. The contents of these applications are each incorporated herein by reference in their entirety.

FIELD OF THE INVENTION

The present invention relates to an apparatus for automatically measuring an analyte concentration in a liquid sample and more particularly for automatically measuring the analyte concentration in the liquid sample and determining a criticality of an interferent, and furthermore relates to a corresponding method and computer program product.

BACKGROUND OF THE INVENTION

Determining a concentration of an analyte in a liquid sample is relevant in numerous applications, e.g., diagnostic testing of blood samples, gaining information from a blood sample into parameters indicative of training status or nutritional quality, and/or testing for certain substances in a blood sample, such as alcohol, narcotics or performance enhancing drugs. However, a measured analyte concentration in a sample may deviate from a true concentration, where the true concentration may be understood to be a concentration of said analyte in an object (such as a person from whom the sample was drawn). For example, certain substances, known as interferents, may interfere with the measurement of a concentration of an analyte, leading to erroneous measurements of the concentration of the analyte, possibly even to a significant level. In consequence, the interference may lead to erroneous results of measurements of concentration of an analyte and/or render resource demanding retesting necessary. As another example, hemolysis release intercellular components (such as components identical to analytes whose concentration in the blood of an object is of interest) from erythrocytes into the plasma phase of a blood sample, which can interfere, e.g., with measurements of concentration of a number of analytes in a blood sample in the sense that the measured concentrations in the sample deviate from true concentrations in the object.

SUMMARY OF THE INVENTION

It is an object of embodiments of the invention to provide an improved apparatus, method and computer program product for automatically measuring an analyte concentration in a liquid sample comprising cell-free hemoglobin, and in particular to provide an apparatus, method and computer program product for automatically measuring an analyte concentration in a liquid sample comprising cell-free hemoglobin, which can mitigate or eliminate negative effects of erroneous results of measurements of concentration of an analyte and/or which can at least partially render a need of retesting superfluous.

According to a first aspect, the invention provides an apparatus for automatically measuring an analyte concentration in a liquid sample comprising the analyte and cell-free hemoglobin and for automatically determining a cell-free hemoglobin interference criticality, said apparatus comprising:

one or more sensors for measuring:
        the analyte concentration in the liquid sample, and
        a cell-free hemoglobin concentration in the liquid sample,
    a data processing device comprising a processor configured to:
        determine the cell-free hemoglobin interference criticality based on:
        the cell-free hemoglobin concentration, and
        the analyte concentration, and
        output a signal indicative of the cell-free hemoglobin interference criticality at least in case the cell-free hemoglobin interference criticality is within a predetermined range.

A possible advantage of the invention is that by basing the cell-free hemoglobin interference criticality on both cell-free hemoglobin concentration and the analyte concentration the data processing device can take into account predetermined instructions in the determination of the cell-free hemoglobin interference criticality (such as predetermined instructions entailing a non-constant, such as a non-linear, relation between the cell-free hemoglobin interference criticality and the analyte concentration), which in turn enables improving the applicability of the cell-free hemoglobin interference criticality.

For example, the invention renders it possible for the cell-free hemoglobin interference criticality to not only be dependent on either of the cell-free hemoglobin concentration and the analyte concentration, which in either case could yield both too high and too low cell-free hemoglobin interference criticality in various scenarios. For a cell-free hemoglobin interference criticality being dependent on only one of cell-free hemoglobin concentration and the analyte concentration, the cell-free hemoglobin interference criticality could be too high for some values of the other concentration and too low for other values of the other concentration. Hence a trade-off would have had to be made between having too many instances of too high cell-free hemoglobin interference criticality values and too many instances of too low cell-free hemoglobin interference criticality values. With the present invention the determination of the cell-free hemoglobin interference criticality can be improved or optimized for any pair or values of analyte concentration and cell-free hemoglobin concentration.

The invention may be advantageous as support for a decision, e.g., on how to react to a certain measured concentration of the analyte, such as supporting said decision in a fast, predetermined, systematic and/or error-free manner, and/or in a manner not requiring expert skills (which may be particularly relevant in, e.g., a point-of-care context).

By 'apparatus for automatically measuring an analyte concentration in a liquid sample' may be understood any apparatus capable of automatically—such as without necessitating human intervention subsequent to providing the liquid sample to the apparatus—measuring an analyte concentration in a liquid, such as in a liquid sample, such as an apparatus capable of probing optical, electrical and/or other properties of a liquid and/or analytes in a liquid and deriving information about analyte concentration.

By 'analyte' is understood any entity, substance or composition, and may in particular be an element, ion and/or molecule. 'Analyte' is understood to encompass a group of analytes, or a group of entities, substances or compositions, such as a group of entities, substances or compositions sharing one or more properties, such as chemical properties or structure or physical properties.

'Cell-free hemoglobin' (cfHb) is understood as is common in the art, and in particular as hemoglobin outside of the red blood cells.

Cell-free hemoglobin (also called naked hemoglobin) is hemoglobin that is not enclosed in the red blood cell. Cell-free hemoglobin may be released into blood plasma, as a result of hemolysis, which is the rupturing (lysis) of red blood cells (erythrocytes) and the release of their contents (cytoplasm) into surrounding fluid (e.g. blood plasma). Hemolysis may occur in vivo or in vitro (inside or outside the body).

By 'cell-free hemoglobin interference' is understood the effect or impact that cell-free hemoglobin in a liquid sample has or can have or can be or is representative of on the measured concentration of the analyte, such as the relative or absolute change (such as with the same unit or unitage as the analyte concentration) in concentration of the analyte (where the change in concentration may be given as the difference between the measured concentration—being influenced by interference—and a true concentration or an estimate of the true concentration, optionally obtained by deducting an estimated contribution from interference), and/or the effect or impact that cell-free hemoglobin in a liquid sample is indicative of with respect to another sought-after concentration, such as a concentration of the sample at an earlier time (such as in the patient and/or before ex vivo/in vitro hemolysis). The effect of the interferent may be due to the inability of the sensor to distinguish the analyte and the interferent and hence the sensor erroneously ascribing the measured contribution from the interferent to the analyte, and hence providing a concentration being rather based on interference and true analyte concentration than on true analyte concentration alone. However, the effect of the interferent may also be due to the interferent being (homologously) linked to an interfering amount of the analyte (which is thus present in the liquid sample, but which should nonetheless be disregarded for the purpose of estimating the true analyte concentration, but which the sensor will for natural reasons take into account). For example, the analyte concentration (such as an potassium ion concentration) to be determined in a blood sample may be the in vivo analyte concentration (i.e., e.g., the analyte concentration in the person from whom a blood sample is drawn), but cell-free hemoglobin may be (homologously) linked with an amount of analyte (such as potassium ions) released into a blood sample subsequent to withdrawal of the blood sample, and hence the measured (and actual, real) concentration of potassium ions in the blood sample will overestimate the true, in vivo analyte concentration (of potassium ions).

'Interference' is thus understood as is common in the art, such as encompassing but not limited neither one entity interfering with the measurement of a concentration of another entity nor one entity being representative of a change of a concentration of another entity with respect to an earlier (sought-after) concentration of that other entity.

In embodiments (such as embodiments wherein the analyte is the potassium ion), 'interference' is understood to be related to one entity being representative of a change of a concentration of another entity with respect to an earlier (sought-after) concentration of that other entity. In, e.g., these embodiments the cell-free hemoglobin interference criticality may be exchanged with, e.g., 'cell-free hemoglobin homology (effect) criticality'.

Besides releasing hemoglobin to the surrounding liquid, hemolysis may additionally release other substances, such as analytes. Thus, if hemolysis takes place outside the body, then a measurement of concentration of such substance(s) (analyte(s)) may not be representative of a true value of a concentration in the person (patient) from whom the sample was originally drawn.

Throughout this application, this effect is for convenience referred to as interference. However, for completeness, it is noted that according to embodiments of the present invention, the 'interference' is not interference in the sense that a measured concentration of a sample is erroneous with respect to a true concentration of the analyte in the sample due to interference because hemoglobin is not as such disturbing (interfering with) the measurement of the true concentration of the analyte, it is merely indicative of the true sample concentration (possibly) being different with respect to the true patient concentration. For this reason, the use of 'interference (criticality)' in this application and throughout this application (except in the present paragraph) could in the context of those embodiments (such as for the 'interference' of cell-free hemoglobin with respect to potassium) be exchanged with 'homology effect (criticality)', such as 'cell-free hemoglobin homology effect (criticality)', e.g., with a view to indicate that the measured analyte concentration in the sample does not necessarily deviate from the true sample concentration, yet due to the homology (described in further detail below) the measured analyte concentration in the sample may deviate from a true patient concentration.

By 'cell-free hemoglobin interference criticality' is understood a measure of the extent to which cell-free hemoglobin interference is critical for estimating a true, such as true value in the liquid sample or true value of the liquid sample prior to a disturbance (such as in a patient from whom the sample is drawn or originates), analyte concentration (based on the measured analyte concentration) and/or for enabling a meaningful use or interpretation of the analyte concentration, such as critical with respect to using the analyte concentration for estimating a parameter (such as morbidity or mortality). For example, the predetermined instructions may be arranged so as to assess cell-free hemoglobin interference criticality based on a ratio or comparison between estimated cell-free hemoglobin interference and analyte concentration (e.g., a cell-free hemoglobin interference threshold can be expressed as a percentage of analyte concentration), e.g., a low analyte concentration yields a high cell-free hemoglobin concentration, whereas a high analyte concentration yields a low cell-free hemoglobin interference criticality. Alternatively, such as according to possibly more advanced predetermined instructions, the predetermined instructions may require that cell-free hemoglobin interference criticality is exclusively low' for an impact of the cell-free hemoglobin interference on the parameter being below a certain impact value (and otherwise, i.e., for said impact being equal to or exceeding said impact value, the cell-free hemoglobin interference criticality is exclusively is 'high'), which entails that cell-free hemoglobin interference criticality depends on the difference in parameter with and without (estimated) cell-free hemoglobin interference.

A cell-free hemoglobin interference threshold can be expressed as a fraction or percentage of analyte concentration, and can with respect to analyte concentration be non-linear or linear, such as constant or non-constant, such as directly proportional or off-set.

Alternatively, a cell-free hemoglobin interference threshold can be expressed in absolute terms, and can with respect to analyte concentration be non-linear or linear, such as constant or non-constant, such as directly proportional or off-set.

A (functional) relation between the parameter and the analyte concentration may be non-constant, such as non-linear.

By 'non-linear' is in the context of the present application generally understood a relation between entities, such as x and y, which cannot be represented on the form y=ax where a is a constant, such as cannot be represented on the form y=ax+b where a and b are constants. For example, y can be a cell-free hemoglobin interference threshold value (for comparison with a cell-free hemoglobin interference for the purpose of assessing cell-free hemoglobin interference criticality) and x can be an analyte concentration.

The cell-free hemoglobin interference criticality can be qualitative, such as binary, e.g., providing a sample space with two and only two mutually exclusive categories (or possible outcome values), e.g., 'high' and 'low', '0' and '1' or 'release' (e.g., providing instructions to release the analyte concentration for clinical diagnosis) or 'retest' (such as instructions to retest due to the risk associated with cell-free hemoglobin interference being too high).

Alternatively, the cell-free hemoglobin sample space can be according to an ordinal type measurement scale (where measurements may be sorted into ranked groups, e.g., into 3 or 4 or 5 or more groups (or outcome values) associated with increased cell-free hemoglobin interference criticality), or an interval or ratio type measurement scale where the cell-free hemoglobin interference criticality may be quantified, such as given a numerical score, such as said numerical score being objectively calculated based on the measured concentrations (and optionally further values according to the predetermined instructions). For example, the cell-free hemoglobin interference criticality can be expressed as a (such as any) real or integer number within an interval, e.g., [0; 100], with lower numbers indicative of a lower criticality and increasingly higher numbers indicative of increasing criticality.

The 'cell-free hemoglobin interference criticality' is to be understood as interchangeable with 'a measure, such as a 'criticality measure' or 'analyte specific criticality measure' or a 'decision support measure' or a 'decision determining measure', being determined according to predetermined instructions and on the basis of the analyte concentration and the cell-free hemoglobin concentration.

The predetermined instructions may comprise information determining how to determine the cell-free hemoglobin interference criticality based on the cell-free hemoglobin concentration, and the analyte concentration.

The data processing device comprises or has access to (e.g., via a digital storage device operatively comprised within the data processing device and/or connected to the processor) predetermined instructions, such as enabling the data processing device to take as input the cell-free hemoglobin concentration and the analyte concentration and determine the cell-free hemoglobin interference criticality based on the cell-free hemoglobin concentration and the analyte concentration according to the predetermined instructions. Alternatively, the predetermined instructions can be implemented as or based on an algorithm or a look-up table. The predetermined instructions can for example be implemented as a cell-free hemoglobin threshold being dependent on the analyte concentration, such as wherein said threshold is implemented as a function of the analyte concentration, wherein cell-free hemoglobin interference criticality depends in a binary manner on whether the measured cell-free hemoglobin exceeds said threshold. Alternatively, the predetermined instructions can be implemented as an algorithm or a look-up table taking as input the analyte concentration and the cell-free hemoglobin concentration and outputting the cell-free hemoglobin interference criticality as a real number (where the sample space with the possible number of outcomes being at least 3, such as at least 10, such as at least 100, such as at least 1000).

The predetermined instructions can be arranged so that a relation between cell-free hemoglobin interference criticality and both of (measured) analyte concentration and (measured) cell-free hemoglobin concentration is non-constant, such as non-linear. The predetermined instructions can be arranged so that the cell-free hemoglobin interference criticality cfHbic is given by or can be described by a function cfHbic=f(cA, ccfHb) being dependent on analyte concentration cA and cell-free hemoglobin concentration ccfHb, where one or more contour lines of said of said function f(cA, ccfHb) are non-linear.

The predetermined instructions can reflect or incorporate a certain categorization or parameterization of analyte concentrations with respect to a parameter and one or more rules for determining cell-free hemoglobin interference criticality based thereon. For example the predetermined instructions can be based on a categorization of analyte concentrations into a number parameter categories, e.g., N categories according to parameter values {1, . . . , N} and a rule for determining cell-free hemoglobin interference criticality can, e.g., state that the cell-free hemoglobin interference criticality is high if an estimated cell-free hemoglobin interference can cause a categorization based directly on measurements on the liquid sample to change by at least two categories compared to a categorization based on the true analyte concentration, such as measurement on the liquid sample where the effect of cell-free hemoglobin interference is estimated and an estimate of a true analyte concentration is based on the measured analyte concentration and the estimated cell-free hemoglobin interference.

The categorization or parameterization can be according to clinical assessments, such as categorization into categories ranked according to morbidity and/or mortality. A rule, which is underlying instructions, based thereon may serve to reduce a risk of misdiagnosing, such as in particular misdiagnosing in a direction increasing a risk of false categorization (such as the—particularly relevant case—where a false categorization erroneously indicates that, e.g., a morbidity and/or mortality is lower than it actually is), based on a particular measured analyte concentration and a particular cell-free hemoglobin concentration.

By 'automatically determining a cell-free hemoglobin interference criticality' is understood, that the apparatus is capable of automatically—such as without necessitating human intervention subsequent to providing the liquid sample to the apparatus—measuring the analyte concentration and the cell-free hemoglobin concentration in the liquid sample, and take the analyte concentration and the cell-free hemoglobin concentration as input (and possibly have, access or otherwise take as input other information, such as predefined instructions) and provide as output the cell-free hemoglobin interference criticality.

'Sensor' is understood as is common in the art and may for example by an ion selective electrochemical sensor, such as a potentiometric sensor.

By 'measuring concentration' is to be understood quantitatively measuring concentration, such as measuring a molar concentration.

'Data processing device' is understood as is common in the art, and in particular as any device capable of receiving, processing and outputting digital information.

'Processor' is understood as is common in the art and in particular electronic circuitry capable of executing instructions that make up a computer program, such as a processing unit, such as a central processing unit (CPU).

By having the data processing device being arranged to determine the cell-free hemoglobin interference criticality based on the cell-free hemoglobin concentration, and the analyte concentration, it is understood that the cell-free hemoglobin interference criticality can change value with a change in value of either of the two concentrations, at least for one or more values of the other concentration.

'Output a signal' is understood as is common in the art, such as providing externally to the data processing device information indicative of the cell-free hemoglobin interference criticality. The format of the output and the signal may take different forms, e.g., as a digital or analog signal. For example, the output of a signal may be digital information representative of the cell-free hemoglobin interference criticality in quantitative or qualitative form. In another example, the output of a signal is a visual and/or audible signal.

By outputting a signal 'at least in case the cell-free hemoglobin interference criticality is within a predetermined range' it may be understood that the signal may in some embodiments be output regardless of the value of the cell-free hemoglobin interference criticality. In other embodiments it is only output if the cell-free interference criticality is within a predetermined range, such as 'high' or 'above 50' alternatively low' or 'equal to or below 50'. It is thus encompassed that the signal is output regardless or the value of the cell-free hemoglobin interference criticality, that it is output only for cell-free hemoglobin criticality being above a certain cut-off value (such as only telling a user, or raising a flag or suggesting to retest, if cell-free hemoglobin criticality is high) or that it is output only for cell-free hemoglobin criticality being below a certain cut-off value (such as only telling a user if cell-free hemoglobin criticality is low).

It may be seen as an advantage of the present invention, that a decision (support) or suggestion (based on measured concentrations) on whether or not to use (release) a measured analyte concentration or not use it (and instead retest), may effectively be determined/taken in advance, such as centrally, such as by qualified personnel with ample time, rather than relying on possibly less qualified personnel having possibly very little time available to make a correct decision.

In an embodiment, there is presented an apparatus arranged for receiving the liquid sample in the form of a whole blood sample comprising red blood cells at a sample inlet, such as a single sample inlet, and for measuring at least the cell-free hemoglobin concentration in at least a portion of the liquid sample comprising or being in liquid connection with the red blood cells. For example, the apparatus comprises a sample inlet, such as exclusively a single sample inlet, arranged for receiving a whole blood sample and for (micro-)fluidically handling that sample to measurement setup(s)/sensor(s) for measuring both of the analyte concentration and the cell-free hemoglobin concentration, such as both concentrations being determined on the same (part) of the liquid sample, i.e., the part for which the analyte concentration in the liquid sample is determined is identical to or in liquid connection with the part for which a cell-free hemoglobin concentration is determined. An advantage of this may be, that only a single liquid sample is needed and/or only a single sample inlet. Furthermore, it may be advantageous, that the sample need not be split into separate parts not being in liquid connection, which may in turn be beneficial for reducing requirements in both space and time, e.g., there is no need to distance parts of the sample not being in liquid connection with each other and/or there is no need to spend time on (liquid) separation of different parts of the sample. Furthermore, the apparatus, such as the (micro-)fluidic handling may be kept simpler. In one embodiment, an issue of red blood cells affecting measurement of cell-free hemoglobin concentration in the liquid sample is overcome by measuring on a portion of the sample being positioned, such as by diffusion and/or capillary forces, in pores of a porous element.

In an embodiment, there is presented an apparatus further arranged for measuring at least the analyte concentration in at least the same portion of the liquid sample for which the cell-free hemoglobin concentration was measured and/or a portion of the sample being in liquid connection with at least the portion of the liquid sample for which the cell-free hemoglobin concentration was measured. This may be advantageous for reducing complexity, and requirements in terms of space and time (cf., the comments made above).

In an embodiment, there is presented an apparatus arranged for measuring the analyte concentration in the liquid sample and the cell-free hemoglobin concentration in the liquid sample at spatial positions being less than 1 m, such as less than 75 cm, such as less than 50 cm, such as less than 25 cm, such as less than 10 cm, such as less than 1 cm, from each other, such as wherein a largest dimension of the apparatus is equal to or less than 2 m, such as equal to or less than 1 m, such as equal to or less than 75 cm. An advantage of this may be that a relatively small apparatus may enable otherwise unrealistic applications, such as point of care (POC) applications and/or applications where the apparatus is to be moved, e.g., on short notice and optionally by a single person between measurements. A relatively small size may enable providing the apparatus or apparatuses closer to patients, which may in turn enable reducing the time and in general the influence on a blood sample drawn from a patient before the sample is provided to the apparatus and subjected to measurements, which may in turn enable more precise results (such as because the blood sample has changed less away from true values).

In an embodiment, there is presented an apparatus arranged for receiving the liquid sample in the form of a whole blood sample comprising red blood cells at a sample inlet at a first point in time t1 and to output at a second point in time t2 the signal indicative of the cell-free hemoglobin interference criticality at least in case the cell-free hemoglobin interference criticality is within a predetermined range, and wherein a period of time between the first point in time and the second point in time is equal to or less than 10 minutes, such as equal to or less than 5 minutes, such as equal to or less than 2 minutes, such as equal to or less than 1 minute, such as equal to or less than 45 seconds, such as equal to or less than 35 seconds, such as equal to or less than 30 seconds, such as equal to or less than 10 seconds. An advantage of this may be that the apparatus enables saving valuable time. Another possible advantage is that reducing the time and thus in general the influence on a blood sample drawn from a patient before the sample is subjected to measurements, may enable more precise results (such as because the blood sample, such as measurable values thereof, has changed less with respect to true values).

In an embodiment, there is presented an apparatus further comprising a porous element, such as a porous mirror, and being arranged for measuring at least the cell-free hemoglobin concentration in a portion of the liquid sample being positioned in one or more pores of porous element.

According to an embodiment, the apparatus comprises an optical measurement setup, such as comprising a porous mirror (PM), arranged for measuring the cell-free hemoglobin concentration in the liquid sample, and/or an electro-analytical measurement setup, such as an ion selective electrode sensor, such as an ion selective electrode membrane sensor, for measuring the analyte concentration (where the analyte concentration may in general be understood to be the analyte concentration in the extracellular phase).

In an embodiment, the analyte concentration is a concentration of potassium ions, such as $K^+$ ions. In, e.g., a blood sample, a departure from a predetermined range could be associated with significant morbidity and mortality, and hence it might be advantageous to obtain the concentration of potassium ions and furthermore the cell-free hemoglobin interference risk criticality, e.g., to support a decision on how to react to a measured potassium ion concentration.

In an embodiment, there is presented an apparatus wherein the data processing device is configured to determine the cell-free hemoglobin interference criticality by:
determining a cell-free hemoglobin interference threshold value based on the analyte concentration,
determining a cell-free hemoglobin interference value based on the cell-free hemoglobin concentration,
comparing:
the cell-free hemoglobin interference value, to
the cell-free hemoglobin interference threshold value, and
determining the cell-free hemoglobin interference criticality based on a result of the comparison.

A possible advantage of determining and comparing based on a cell-free hemoglobin interference threshold value may be that it takes into account the actual and/or estimated interference value, such as the actual and/or estimated effect on the analyte concentration, which may be seen as the most relevant parameter.

In an embodiment, there is presented an apparatus wherein the cell-free hemoglobin interference threshold value based on analyte concentration is an absolute value, such as wherein a function describing the cell-free hemoglobin interference threshold value as a function of the analyte concentration is non-linear. A possible advantage of using the absolute value may be that it is relatively simple. A possible advantage of having said function being non-linear, may be that it enables more accurately tailoring it to a clinically relevant picture.

In an embodiment, there is presented an apparatus wherein the cell-free hemoglobin interference threshold value based on analyte concentration is a relative value being relative with respect to the analyte concentration, such as wherein a function describing the cell-free hemoglobin interference threshold value as a function of the analyte concentration is non-constant, such as non-linear. A possible advantage of using the relative value may be that it enables in a relatively simple manner taking the analyte concentration into account, such as scaling with respect to the analyte concentration. A possible advantage of having said function being non-constant, such as non-linear, may be that it enables more accurately tailoring it to a clinically relevant picture.

In an embodiment, the data processing device is configured to determine the cell-free hemoglobin interference criticality by:
determining a cell-free hemoglobin concentration threshold value based on the analyte concentration,
comparing:
the cell-free hemoglobin concentration or a parameter based on the cell-free hemoglobin concentration, such as cell-free hemoglobin interference, to
the cell-free hemoglobin concentration threshold value, and
determining the cell-free hemoglobin interference criticality based on a result of the comparison.

This embodiment may be advantageous due to the simplicity offered by having a threshold. For example, according to predetermined instructions each analyte concentration may be associated with a tolerance towards cell-free hemoglobin or a parameter based on the cell-free hemoglobin concentration (e.g., corresponding to an acceptable amount of cell-free hemoglobin or cell-free hemoglobin interference), which is implemented in the data processing device as a threshold for cell-free hemoglobin and/or cell-free hemoglobin interference, such as a non-constant, and optionally non-linear, threshold, which can be compared with the cell-free hemoglobin concentration or cell-free hemoglobin interference to provide the cell-free hemoglobin interference criticality based on the comparison, e.g., resulting in an output signal comprising information, such as according to one option "above" or "below" or according to another option a real number indicating a signed difference between the threshold and the cell-free hemoglobin concentration or a parameter based on the cell-free hemoglobin concentration.

A possible advantage of determining and comparing based on a cell-free hemoglobin concentration threshold value may be that it is relatively simple, such as does not necessitate estimating an interference value.

The 'cell-free hemoglobin concentration threshold value' may be expressed as a relative or absolute (such as with the same unit or unitage as the ccfHb or analyte concentration) value, where a relative value may be expressed relative to a concentration of the analyte.

A cell-free hemoglobin concentration threshold can be expressed as a fraction or percentage of analyte concentration, and can with respect to analyte concentration be non-linear or linear, such as constant or non-constant, such as directly proportional or off-set.

In an embodiment, there is presented an apparatus wherein the cell-free hemoglobin concentration threshold value based on analyte concentration is a relative value being relative with respect to the analyte concentration, such as wherein a function describing the cell-free hemoglobin concentration threshold value as a function of the analyte concentration is non-constant, such as non-linear. A possible advantage of using the relative value may be that it enables in a relatively simple manner taking the analyte concentration into account, such as scaling with respect to the analyte concentration. A possible advantage of having said function being non-constant, such as non-linear, may be that it enables more accurately tailoring it to a clinically relevant picture.

Alternatively, a cell-free hemoglobin concentration threshold can be expressed in absolute terms, and can with respect to analyte concentration be non-linear or linear, such as constant or non-constant, such as directly proportional or off-set.

In an embodiment, there is presented an apparatus wherein the cell-free hemoglobin concentration threshold value based on analyte concentration is an absolute value, such as wherein a function describing the cell-free hemoglobin concentration threshold value as a function of the analyte concentration is non-linear. A possible advantage of using the absolute value may be that it is relatively simple. A possible advantage of having said function being non-linear, may be that it enables more accurately tailoring it to a clinically relevant picture.

The cell-free hemoglobin concentration threshold value may be determined based on (1) literature values for hemolysis detection and/or (2) a model relating the analyte concentration to a parameter (such as a model attributing particular clinical pictures to ranges of analyte concentration) with a rule, e.g., that it is acceptable that interference can move categorization of a liquid sample across a border from one category to another but it is not allowed to bypass a category (i.e., move across an entire category/two borders).

In a further embodiment there is presented an apparatus wherein the cell-free hemoglobin threshold value is a function of the analyte concentration, and wherein the function is non-constant with respect to analyte concentration, such as increasing with increasing analyte concentration or decreasing with increasing analyte concentration, such as a result of the function numerically changing with increasing analyte concentration, within at least one analyte concentration interval, such as strictly increasing within at least one analyte concentration interval having an extent larger than zero (such as excluding functions, which are non-constant exclusively due to differences in values between piecewise constant segments, such as excluding (Heaviside) step functions). In embodiments, the function is neither strictly increasing nor strictly decreasing (such as having one or more local minima and/or one or more local maxima).

By having a non-constant relation between the cell-free hemoglobin threshold value and the analyte concentration, it can be taken into account that a certain (relatively high) cell-free hemoglobin concentration is not necessarily critical or detrimental (for subsequent use, such as for subsequent decision making) for all analyte concentrations and simultaneously that another certain (relatively low) cell-free hemoglobin concentration may be critical or detrimental (for subsequent use, such as for subsequent decision making) for some analyte concentrations.

It is understood that 'the cell-free hemoglobin threshold value is a function of the analyte concentration' implies that the cell-free hemoglobin threshold value (for a given analyte concentration) can be determined as a (or via a threshold-) function of the analyte concentration.

In another further embodiment there is presented an apparatus wherein the cell-free hemoglobin threshold value is a function of the analyte concentration, wherein the function is non-linear with respect to analyte concentration, such as increasing with increasing analyte concentration or decreasing with increasing analyte concentration, such as a result of the function numerically changing with increasing analyte concentration, within at least one analyte concentration interval, such as strictly increasing within at least one analyte concentration interval having an extent larger than zero. By having a non-linear relation between the cell-free hemoglobin threshold value and the analyte concentration, more complex (such as non-linear) situations can be taken into account, such as more complex (such as non-linear) relations between a parameter and the analyte concentration.

For example, a predetermined effect of an error in the analyte concentration (due to the measured analyte concentration deviating from the true analyte concentration as a result of cell-free hemoglobin interference) on the parameter (determined by the measured analyte concentration) may be tolerated. By having a non-linear relation between the threshold value and the analyte concentration, it is possible to take into account a non-linear relation between the parameter and the analyte concentration (and still be able to determine the cell-free hemoglobin interference criticality in accordance with the tolerance level across the analyte concentrations). This may be seen as highly beneficial, e.g., with a view to neither determining too high criticality values in situations where the parameter does not change much with an (interference) error nor determining too low criticality values in situations where the parameter changes a lot with an (identically sized interference) error.

Advantages mentioned above for the non-constant and non-linear thresholds applies as well, mutatis mutandis, to embodiments without a threshold.

According to an embodiment, the data processing device is operatively connected to a storage device comprising:

a predetermined categorization scheme, such as wherein the predetermined categorization scheme enables categorizing (such as categorizing into a particular clinical picture) liquid samples based on analyte concentration, and wherein the data processing device is configured to determine the cell-free hemoglobin interference criticality by:

Determining a measured category of the liquid sample based on the analyte concentration (such as the (raw) measured analyte concentration not being adjusted for the interference effect of the cell-free hemoglobin), such as attributing the analyte concentration to a measured particular clinical picture, Determining an adjusted concentration, such as an adjusted analyte concentration, wherein the adjusted concentration is based on the analyte concentration, such as the (raw) measured analyte concentration, adjusted for an interference effect of the cell-free hemoglobin, wherein the interference effect of the cell-free hemoglobin is based on the cell-free hemoglobin concentration, Determining an adjusted category of the liquid sample based on the adjusted concentration, such as attributing the analyte concentration to an adjusted particular clinical picture, and Determining the cell-free hemoglobin interference criticality based on a degree of difference between the measured category and the adjusted category.

An advantage may be that it enables utilizing a predetermined categorization scheme, such as a clinical categorization scheme (such as categorizing into a particular clinical picture) where different ranges of an analyte concentration entails attribution to a particular clinical picture, such as 'life threatening hypokalemia', 'severe hypokalemia', 'moderate hypokalemia', 'normal', 'moderate hyperkalemia', 'severe hyperkalemia', and 'life threatening hyperkalemia'.

According to a further embodiment there is presented an apparatus wherein the cell-free hemoglobin interference criticality is either low or high, and wherein the predetermined categorization scheme is one-dimensional and comprises at least three categories, and wherein the cell-free hemoglobin interference criticality is:

low if the measured category and the adjusted category are identical or adjoining in the predetermined categorization scheme, and high if the unless the measured category and the adjusted category are separated by at least one category in the predetermined categorization scheme (such as wherein there is at least one category between the measured category and the adjusted category).

This embodiment may be advantageous due to the simplicity offered. In an alternative formulation, it is allowed that a step from the measured category to the adjusted category cross from one category to another but it is not allowed that the step bypasses a category.

According to an embodiment, the data processing device is configured to output the signal conditional on the cell-free hemoglobin interference criticality exceeding a cell-free hemoglobin interference criticality threshold. A possible advantage of this embodiment is that a user is only informed (or disturbed) if there is reason to worry about the cell-free hemoglobin interference criticality.

According to another embodiment, the data processing device is configured to output the signal unconditional of the value of the cell-free hemoglobin interference criticality. A possible advantage of this may be that a user can be (explicitly) informed about the cell-free hemoglobin interference criticality.

According to an embodiment, the analyte concentration is a concentration of analytes chosen from the group consisting of:

potassium ions, such as $K^+$ ions,
sodium ions, such as $Na^+$ ions,
calcium ions, such as $Ca^{2+}$ ions,
glucose,
creatinine, and
lactate.

An advantage of this may be that any one of the listed analytes may be relevant for human health, and hence each of their concentrations (in, e.g., a blood sample) and the cell-free hemoglobin interference criticality is relevant for assessment of human health.

According to an embodiment there is presented an apparatus according to any of the preceding claims, wherein the analyte concentration is a plurality of analyte concentrations of analytes, and wherein for at least two of the analytes:

the data processing device is configured to:
determine the cell-free hemoglobin interference criticality based on:
the cell-free hemoglobin concentration, and
the analyte concentration, and
output a signal indicative of the cell-free hemoglobin interference criticality at least in case the cell-free hemoglobin interference criticality is within a predetermined range, and
wherein a relation between the cell-free hemoglobin interference criticality and analyte concentration is different from one analyte to another, such as unique for at least two analytes.

An advantage may be that for multiple ions a signal indicative of the cell-free hemoglobin interference criticality can be output (such a warning a, possibly non-specialized, user that interference is or may be critical). Another possible advantage may be that it can be taken into account, that different analytes may be impacted differently by cell-free hemoglobin (see also inventors' data in TABLES I-II, which clarifies that measurements of different analyte concentrations can be impacted/interfered differently with respect to a certain ccfHb compared to measurements of concentrations of other analytes) and/or that attribution of analyte concentrations to a particular clinical picture may be different for different analytes (e.g., even for a certain level of interference at a certain concentration of each of two analytes, cfHb interference criticality may differ due to said interference might risk changing attribution to a particular clinical picture based on said concentration to a larger degree for one analyte compared to the other). According to an embodiment, cell-free hemoglobin interference criticalities are determined for at least two analytes by calculating a cell-free hemoglobin interference effect for each analyte (i.e., the absolute, quantitative effect the interference has on each analyte, which may vary from analyte to analyte), and wherein the apparatus is arranged so that similarly sized interference effects may result in different cell-free hemoglobin interference criticalities, even in case each of said at least two analytes have the same concentration.

According to an embodiment there is presented an apparatus further comprising a user interface, such as a graphical user interface, arranged for visually outputting information representative of the signal. A possible advantage of this may be that a user can visually observe information representative of the signal. Another possible advantage is that the content of the information, e.g., a cell-free hemoglobin interference criticality value (such as '45.876') and/or guidance on how to proceed (such as 'the cell-free hemoglobin interference criticality exceeds acceptable values—please retest') can be presented to a user, including a non-expert user, allowing the user to obtain the relevant information very fast (e.g., as compared to audibly or digitally outputting the corresponding information).

According to an embodiment there is presented an apparatus further comprising:

a user interface, such as a graphical user interface, arranged for receiving user input, such as a cell-free hemoglobin concentration threshold value for a specific analyte concentration,
wherein the data processing device is configured to:
determine the cell-free hemoglobin interference criticality based on the user input.

A possible advantage may be that a user can provide user input, e.g., complete predefined instructions or merely a cell-free hemoglobin concentration threshold for a specific analyte concentration, and the data processing device can then take this input into account, e.g., according to the predefined instructions or by providing a non-constant cell-free hemoglobin concentration threshold comprising the provided cell-free hemoglobin concentration threshold for the specific analyte concentration. Thus, a user can provide or affect predetermined instructions for how the cell-free hemoglobin criticality is determined, optionally in a semi-automated manner. For example, a lab-manager or point-of-care-test-manager chooses the acceptable detection limit at for a normal sample concentration (e.g., $K^+$ at 4 mM) and then threshold values are automatically decided for all analyte concentrations of K.

According to an embodiment there is presented an apparatus wherein the cell-free hemoglobin interference criticality is determined based on a look-up-table or an algorithm or a function, such as a mathematical function.

According to an embodiment there is presented an apparatus wherein:

for at least one first analyte concentration, a first change in cell-free hemoglobin interference criticality changes with increasing cell-free hemoglobin concentration at a first cell-free hemoglobin concentration, and
for at least one second analyte concentration, a second change in cell-free hemoglobin interference criticality changes with increasing cell-free hemoglobin concentration at a second cell-free hemoglobin concentration, wherein the first change is substantially identical or identical to the second change, such as the first change and the second change each corresponds to exceeding a cell-free hemoglobin threshold value, the first analyte concentration is less than the second analyte concentration, and the first cell-free hemoglobin concentration is different from, such as less than or larger than, the second cell-free hemoglobin concentration.

An advantage of this embodiment may be that changes in cell-free hemoglobin criticality is not confined to take place at a constant analyte concentration.

According to an embodiment there is presented an apparatus, wherein for at least two different analyte concentrations, the cell-free hemoglobin threshold value which is based on the lowest of the two different analyte concentrations, the cell-free hemoglobin threshold value which is based on the highest of the two different analyte concentration.

An advantage of this embodiment may be that the cell-free hemoglobin threshold value is not confined to be constant with respect to analyte concentration.

According to an embodiment there is presented an apparatus, wherein the apparatus, such as said apparatus being a blood gas analyser, is further arranged for measuring a concentration in the liquid sample of one or more or all of:

Carbon dioxide, such as $CO_2$,

Oxygen, such as $O_2$, and pH.

An advantage of having such (blood gas analyzer) apparatus may be that it enables providing further relevant liquid (blood) sample parameters, such as wherein—via the output—a user (even a non-specialized) user may be informed, e.g., if one or more analytes may be associated with a (too) high cell-free hemoglobin interference criticality, such as wherein retesting may be necessary. An advantage may for example be, that it provides a relevant solution for point-of-care testing, where one or more or all of fast response times, relevant output to non-specialized users and a plurality of parameters may be particularly relevant.

According to a second aspect of the invention, there is presented a method for automatically measuring an analyte concentration in a liquid sample comprising the analyte and cell-free hemoglobin and for automatically determining a cell-free hemoglobin interference criticality, said method comprising:

a. measuring the analyte concentration in the liquid sample, b. measuring a cell-free hemoglobin concentration in the liquid sample, c. providing to a data processing device comprising a processor:

the analyte concentration, the cell-free hemoglobin concentration, d. automatically determining with the data processing device the cell-free hemoglobin interference criticality based on:

the cell-free hemoglobin concentration, and the analyte concentration, and e. output from the data processing device a signal indicative of the cell-free hemoglobin interference criticality at least in case the cell-free hemoglobin interference criticality is within a predetermined range.

In an embodiment there is presented a method wherein the determination of cell-free hemoglobin interference criticality is further based on:

a. a predetermined categorization scheme, such as wherein the predetermined categorization scheme enables categorizing liquid samples based on analyte concentration, and wherein the method comprises determining the cell-free hemoglobin interference criticality by:

b. Determining a measured category of the liquid sample based on the analyte concentration, such as attributing the analyte concentration to a measured particular clinical picture, c. Determining an adjusted concentration, such as an adjusted analyte concentration, wherein the adjusted concentration is based on the analyte concentration, such as the measured analyte concentration, adjusted for an interference effect of the cell-free hemoglobin, wherein the interference effect of the cell-free hemoglobin is based on the cell-free hemoglobin concentration, d. Determining an adjusted category of the liquid sample based on the adjusted concentration, such as attributing the analyte concentration to an adjusted particular clinical picture, and e. Determining the cell-free hemoglobin interference criticality based on a degree of difference between the measured category and the adjusted category.

In an embodiment there is presented a method wherein the liquid sample is at least in part, such as in part or in entirety:

a sample comprising cells, such as red blood cells, a sample derived from a sample comprising cells, such as red blood cells, a whole blood sample, such as a human whole blood sample, or a sample derived from a whole blood sample, such as serum or plasma, such as derived from a whole human blood sample, such as being a diluted whole blood sample and/or being a fraction of a whole human blood sample.

An advantage of this embodiment may be that hemolysis may have occurred, which may have caused interference (e.g., by releasing potassium ions into a liquid sample subsequent to withdrawal from a patient), and which can be addressed by determining the cell-free hemoglobin interference criticality.

In an embodiment there is presented a method wherein if the cell-free hemoglobin criticality exceeds a cell-free hemoglobin interference criticality threshold the method further comprises obtaining another liquid sample comprising the analyte and cell-free hemoglobin and repeating steps a-e.

A possible advantage may be that determining the cell-free hemoglobin interference criticality triggers a specific action (which may yield an cell-free hemoglobin interference criticality not exceeding the cell-free hemoglobin interference criticality threshold).

According to a third aspect of the invention, there is presented a computer program, such as a computer program product, comprising instructions which, when the program is executed by a computer, cause the computer to:

receive a first information based on an analyte concentration, receive a second information based on a cell-free hemoglobin concentration, determine a cell-free hemoglobin interference criticality based on:

the cell-free hemoglobin concentration, and the analyte concentration, and output a signal indicative of the cell-free hemoglobin interference criticality at least in case the cell-free hemoglobin interference criticality is within a predetermined range.

According to another aspect, there is presented a computer-readable data carrier having stored thereon the computer program of the third aspect.

According to another aspect, there is presented a data processing apparatus comprising a processor adapted to perform the method of the second aspect and/or being adapted to execute the computer program according to the third aspect.

According to another aspect, there is presented a method for providing predetermined instructions, such as an apparatus and/or a computer program based on said predetermined instructions, said method comprising:

obtaining a predetermined categorization scheme, such as wherein the predetermined categorization scheme enables categorizing liquid samples based on analyte concentration, and for each conceivable pair or analyte concentration and cell-free hemoglobin concentration, determine the cell-free hemoglobin interference criticality by:

Determining a measured category of the liquid sample based on the analyte concentration, such as attributing the analyte concentration to a measured particular clinical picture, Determining an adjusted concentration, such as an adjusted analyte concentration, wherein the adjusted concentration is based on the analyte concentration, such as the measured analyte concentration, adjusted for an interference effect of the cell-free hemoglobin, wherein the interference effect of the cell-free hemoglobin is based on the cell-free hemoglobin concentration, Determining an adjusted category of the liquid sample based on the adjusted concentration, such as attributing the analyte concentration to an adjusted particular clinical picture, Determining the cell-free hemoglobin interference criticality based on a degree of difference between the measured category and the adjusted category, Providing the predetermined instructions as a set of data linking each conceivable pair of analyte concentration and cell-free hemoglobin concentration with the determined cell-free hemoglobin interference criticality, such as a look-up table or an algorithm.

In the context of point-of-care measurement systems (in the art also referred to as 'bedside' systems) and laboratory environments alike, blood gas analysis is oftentimes undertaken by users, such as nurses, who may not be users trained in use of blood gas analyzers and/or interpretation of the results. This may cause unnecessary retesting (e.g., due to users erring on the side of caution for samples where interference may be an issue, even if a correct interpretation would have clarified that retesting would not have been necessary) or erroneously relying on results (which should not have been relied on due to, e.g., a risk of misdiagnosis due to interference), where a correct interpretation would have led to the results not being relied upon.

According to another aspect of the invention, there is presented use of a use of an apparatus according to the second aspect of the invention for point-of-care (POC) for:

determining a cell-free hemoglobin interference criticality based on:

the cell-free hemoglobin concentration, and the analyte concentration, and outputting a signal indicative of the cell-free hemoglobin interference criticality at least in case the cell-free hemoglobin interference criticality is within a predetermined range.

POC measurement is also referred to as 'bed site' measurement in the art. In the present context, the term 'point-of-care measurement' should be understood to mean measurements which are carried out in close proximity to a patient, i.e. measurements that are not carried out in a laboratory. Thus, according to this embodiment, the user of the apparatus, such as the blood gas analyzer, performs measurement of a whole blood sample in a handheld blood sample container in the proximity of the patient, from whom the blood sample is taken, e.g. in the hospital room or ward accommodating the patient's bed, or in a nearby room of the same hospital department. In such use, the level of expertise of the user oftentimes varies from novice to experienced, and the capability of the blood gas analyzer to automatically output instructions matching each individual user's skills on the basis of sensor input is thus particularly beneficial in such environments.

According to an alternative third aspect, there is presented a computer program, such as a computer program product, comprising instructions to cause the apparatus according to the first aspect to execute the steps of the method of the second aspect.

According to a further aspect, there is presented a computer-readable medium having stored thereon the computer program of the third aspect and/or the computer program of the alternative third aspect.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The apparatus, method and computer program product for automatically measuring an analyte concentration in a liquid sample comprising cell-free hemoglobin, according to the invention will now be described in more detail with regard to the accompanying figures. The figures show one way of implementing the present invention and is not to be construed as being limiting to other possible embodiments falling within the scope of the attached claim set.

DETAILED DISCLOSURE OF THE INVENTION

Figure 1:
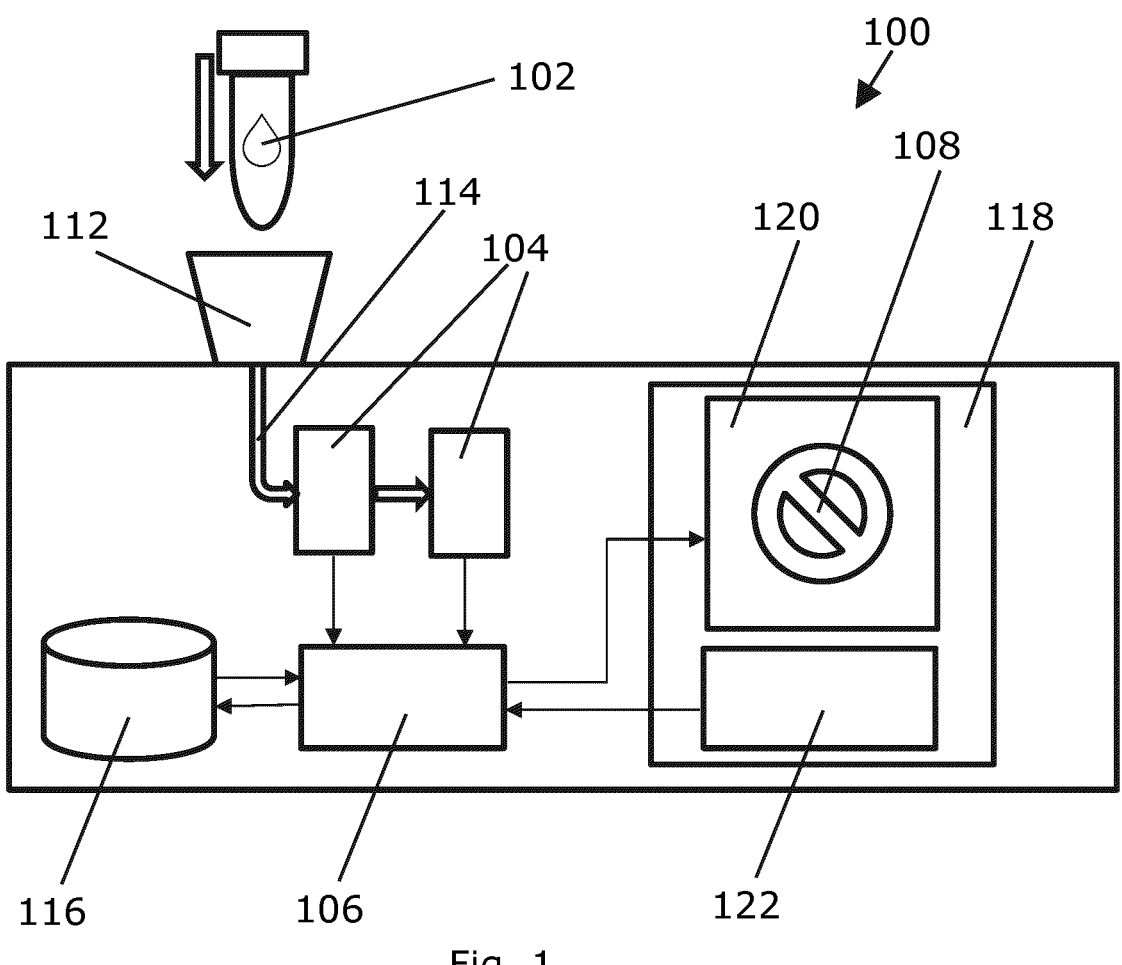
FIG. 1 is a schematic illustration of an apparatus 100 for automatically measuring an analyte concentration in a liquid sample

FIG. 1 is a schematic illustration of an apparatus 100 for automatically measuring an analyte concentration in a liquid sample 102 comprising the analyte and cell-free hemoglobin and for automatically determining a cell-free hemoglobin interference criticality, said apparatus comprising:
    one or more sensors 104 for measuring:
        the analyte concentration in the liquid sample, and
        a cell-free hemoglobin concentration in the liquid sample,
    a data processing device 106 comprising a processor configured to:
        determine the cell-free hemoglobin interference criticality based on:
            the cell-free hemoglobin concentration, and
            the analyte concentration, and
                output a signal 108 indicative of the cell-free hemoglobin interference criticality at least in case the cell-free hemoglobin interference criticality is within a predetermined range.

In the depicted embodiment, the one or more sensors 104 comprise two sensors, one for measuring each of the analyte concentration in the liquid sample, and the cell-free hemoglobin concentration in the liquid sample. The schematic illustration in FIG. 1 furthermore shows a liquid sample inlet 112, a microfluidic system 114, a storage device 116, a user interface 118, wherein the user interface comprises an output unit 120 arranged for visually outputting information representative of the signal (which output unit in the depicted embodiment is a display unit depicting a signal 108 indicating to a user that a cell-free hemoglobin interference criticality exceeds acceptable values and that a warning against proceeding with the measured analyte concentration is issued) and an input unit 122 (such as a keyboard). The thin-line arrows indicate flow of information, such as the analyte concentration in the liquid sample and the cell-free hemoglobin concentration in the liquid sample flowing from the one or more sensors 104 to the data processing device 106, the output signal flowing from the data processing device 106 to the user interface 118 (and more particularly the output unit 120), user input flowing from the input unit 122 to the data processing device 106 (wherein it may be processed so that the data processing device can amend the predetermined instructions in the storage device 116), and predetermined instructions flowing from the storage device 116 to the data processing device 106.

The one or more sensors 104 may comprise a porous element, such as a porous mirror, such as for measuring the cell-free hemoglobin concentration in the liquid sample. In brief the porous mirror (PM) is a technology to provide an optical absorbance measurement of the plasma phase of a whole blood (WB) sample. It can be used to determine the concentration of cell free hemoglobin (ccfHb). In embodiments it functions by allowing ccfHb to diffuse into a porous PETP membrane, with a pore size smaller than the red blood cells (RBCs). RBCs are thus excluded from entering into the pores. The pores are dead-end inside the membrane, so each of the 1.2 million pores per mm$^2$ constitutes a nano-cuvette (ø=400 nm, length=25 µm) in close proximity to the sample. ccfHb and other plasma constituents are transported to and from the nano-cuvettes by diffusion. The front side (facing the sample) of the porous membrane is coated with a noble metal (Pd, thickness=100 nm), but still open at the pore ends facing the sample. The metal layer at the front of the membrane allows for light reflection (the mirror in PM) enabling a transmission-like measurement of the hemoglobin (Hb) inside the pores from the backside of the membrane. Conveniently, optical interferences from Hb in the RBCs in the sample and/or other particulate matter are suppressed to a negligible level by the same optically shielding metal layer. The porous mirror device may be a porous mirror for detection of an analyte in a fluid by optical probing, comprising
    a translucent slab with a front side, and a backside facing away from the front side, wherein the front side is adapted for being contacted with a fluid, and
    a reflective layer at the front side of the translucent slab, the reflective layer being adapted to reflect light reaching the reflective layer from the backside of the translucent slab,
wherein the translucent slab comprises pores, wherein the pores are dead end pores, extending from respective openings at the front side into the translucent slab, through the reflective layer,
wherein a cross-sectional dimension of the openings of the pores is dimensioned so as to prevent larger particles or debris, if any included the fluid, from entering the pores, while allowing the analyte in the fluid to enter the pores via diffusion. The porous mirror (PM) technology is described in WO 2017/085162 A1, which is hereby incorporated in entirety, such as particularly described in claim 1 of WO 2017/085162 A1 and furthermore in FIG. 1 and the accompanying text on pages 24-25.

Figure 2:
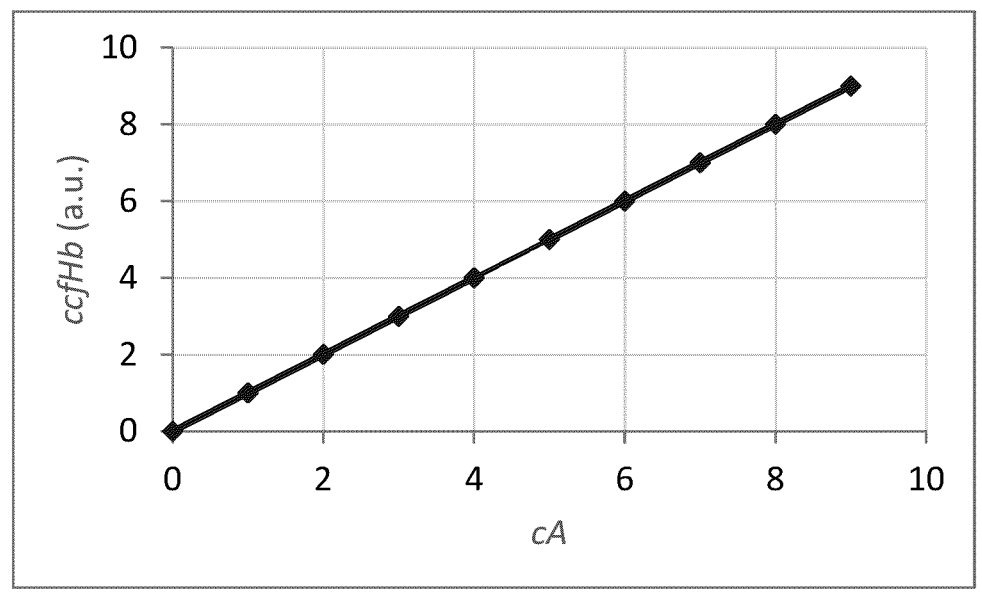
FIG. 2 shows an example of a cell-free hemoglobin concentration (ccfHb) threshold according to predefined instructions according to an embodiment.

FIG. 2 shows an example of a cell-free hemoglobin concentration (ccfHb) threshold according to predefined instructions according to an embodiment, wherein said threshold is non-constant and linear, and in particular directly proportional, with respect to the analyte concentration (cA).

Figure 3:
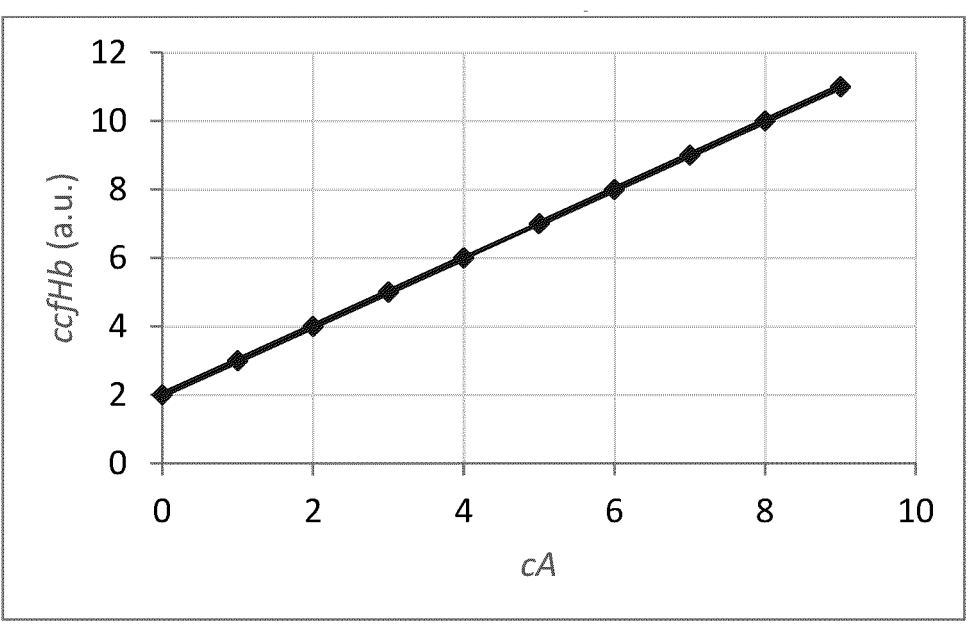
FIG. 3 shows another example of a cell-free hemoglobin concentration (ccfHb) threshold according to predefined instructions according to an embodiment.

FIG. 3 shows another example of a cell-free hemoglobin concentration (ccfHb) threshold according to predefined instructions according to an embodiment, wherein said threshold is non-constant and linear where the threshold is defined by a constant of proportionality k=ccfHb/cA (albeit it is not directly proportional), with respect to the analyte concentration (cA).

Figure 4:
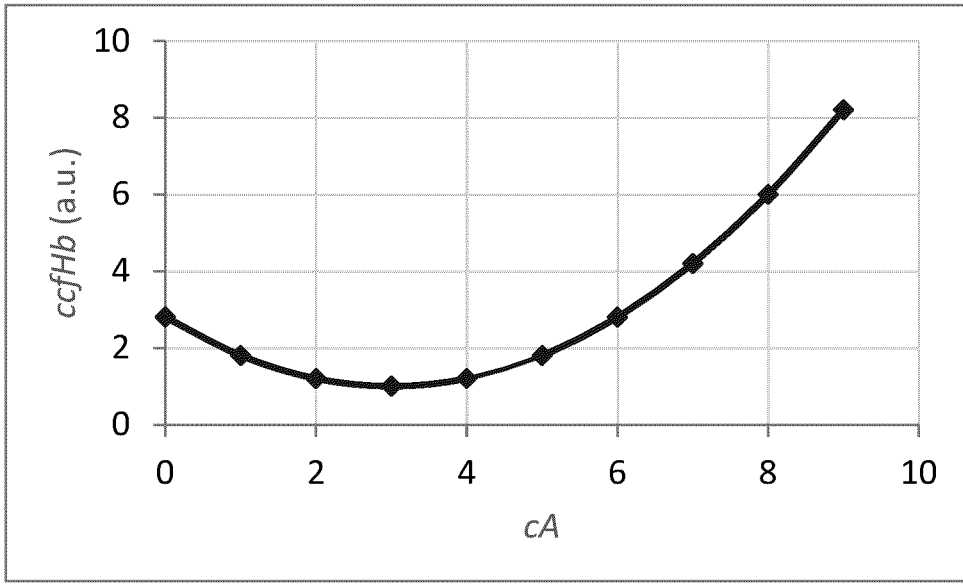
FIG. 4 shows another example of a cell-free hemoglobin concentration (ccfHb) threshold according to predefined instructions according to an embodiment

FIG. 4 shows another example of a cell-free hemoglobin concentration (ccfHb) threshold according to predefined instructions according to an embodiment, wherein said threshold is non-constant and non-linear, i.e., the threshold cannot be defined by a constant of proportionality k=ccfHb/cA with respect to the analyte concentration (cA). In the particular embodiment shown, the relation between values of the threshold and the analyte concentration is defined by a second order polynomial. In the particular embodiment shown, the values of the threshold are neither strictly increasing nor strictly decreasing with respect to the analyte concentration.

Figure 5:
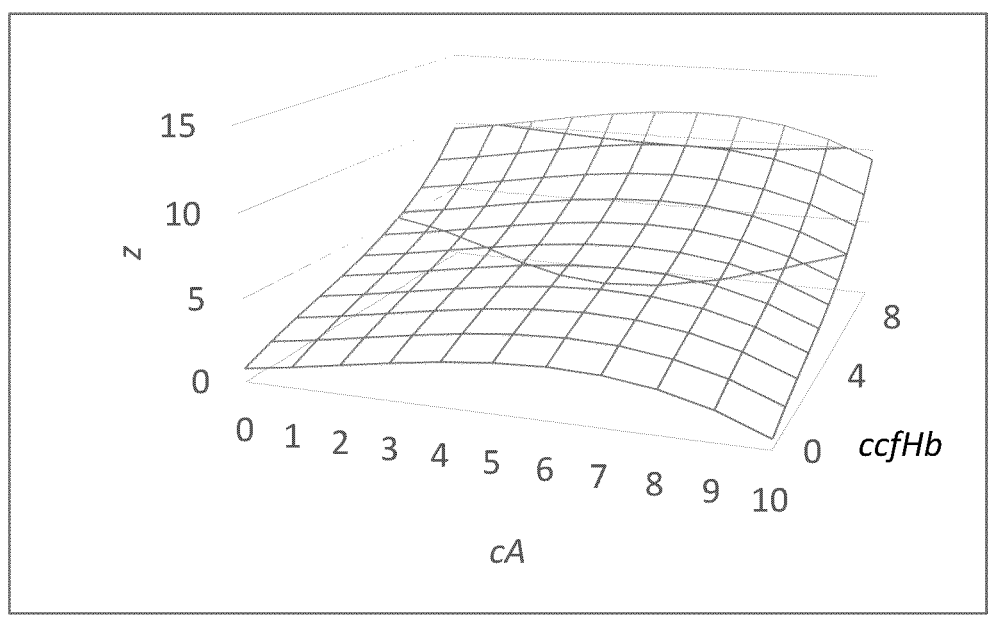
FIG. 5 shows a wireframe 3D surface of a function according to an embodiment
Figure 6:
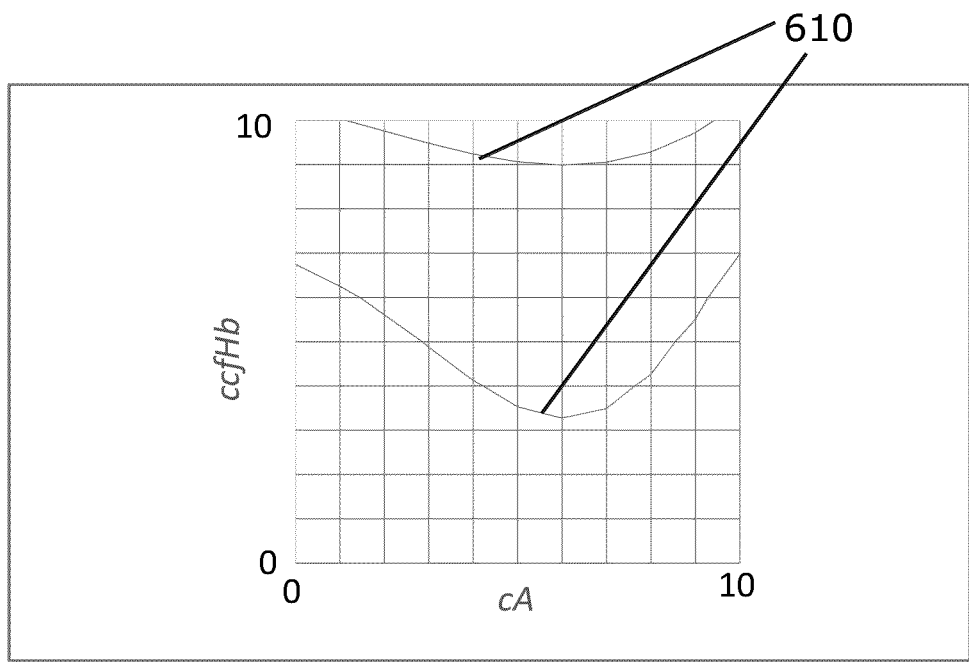
FIG. 6 shows a wireframe contour plot of the function also depicted in FIG. 5

FIGS. 5-6 relate to an embodiment wherein the cell-free hemoglobin interference criticality is determined (quantified) on an interval or ratio scale, such as provided as a real number on a scale from 0 to 15. A function taking as arguments the analyte concentration (cA) and cell-free hemoglobin concentration (ccfHb) and provides as result the cell-free hemoglobin interference criticality (z).

FIG. 5 shows a wireframe 3D surface of a function according to an embodiment wherein the cell-free hemoglobin interference criticality is determined (quantified) by the function as a value on an interval or ratio scale, such as as a real number on a scale from 0 to 15. The function taking as arguments the analyte concentration (cA) and cell-free hemoglobin concentration (ccfHb) and provides as result the cell-free hemoglobin interference criticality (z).

FIG. 6 shows a wireframe contour plot of the function also depicted in FIG. 5, wherein the contour lines 610 are non-linear (i.e., not straight in the figure).

Figure 7:
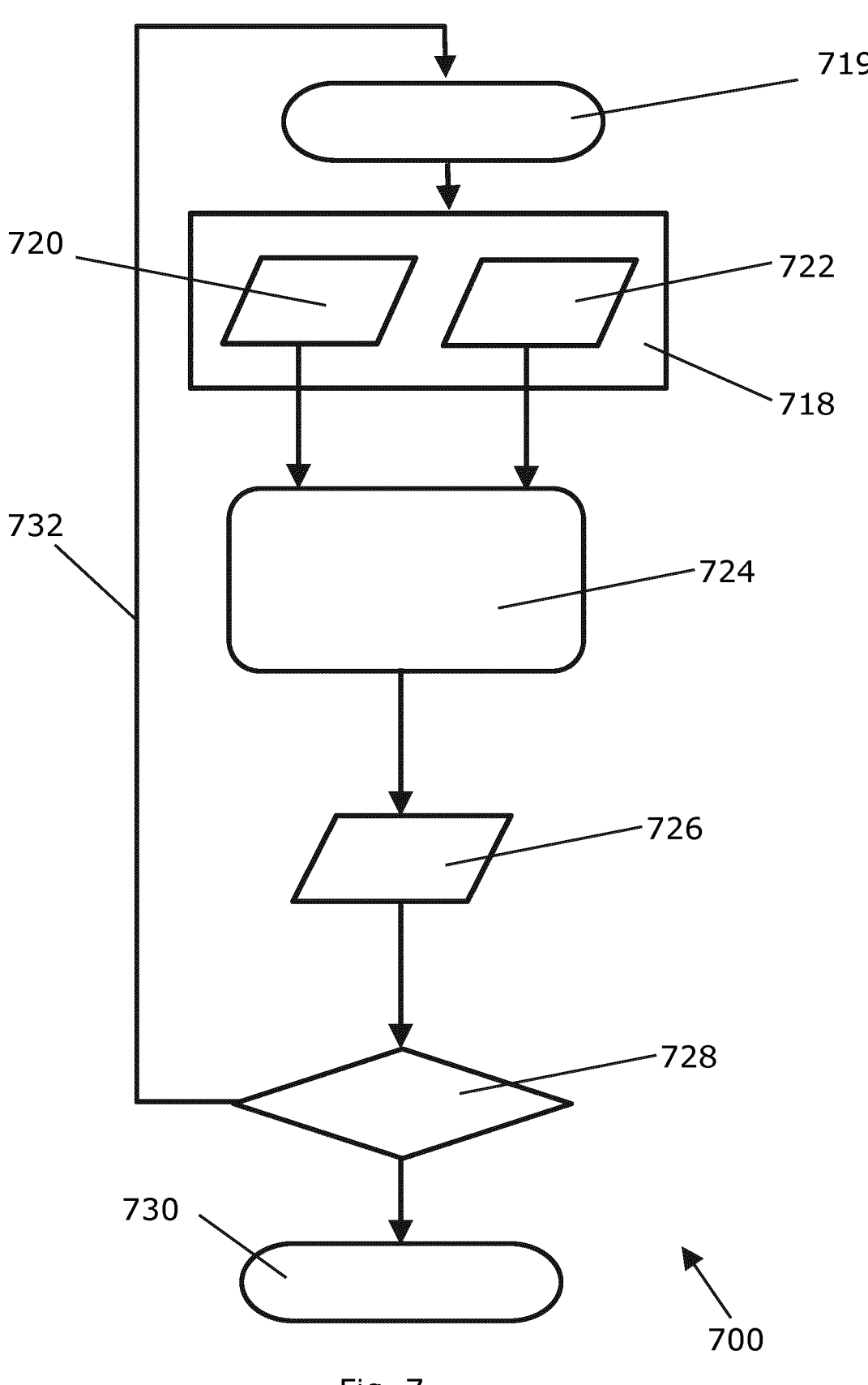
FIG. 7 shows a method 700 for automatically measuring an analyte concentration in a liquid sample 102

FIG. 7 shows a method 700 (starting at block 719) for automatically measuring an analyte concentration in a liquid sample 102 comprising the analyte and cell-free hemoglobin and for automatically determining a cell-free hemoglobin interference criticality, said method comprising:

a. measuring 720 the analyte concentration in the liquid sample, b. measuring 722 a cell-free hemoglobin concentration in the liquid sample, c. providing to a data processing device 106 comprising a processor:

the analyte concentration, the cell-free hemoglobin concentration, d. automatically determining 724 with the data processing device the cell-free hemoglobin interference criticality based on:

the cell-free hemoglobin concentration, and the analyte concentration, and e. output 726 from the data processing device a signal indicative of the cell-free hemoglobin interference criticality at least in case the cell-free hemoglobin interference criticality is within a predetermined range.

Figure 8:
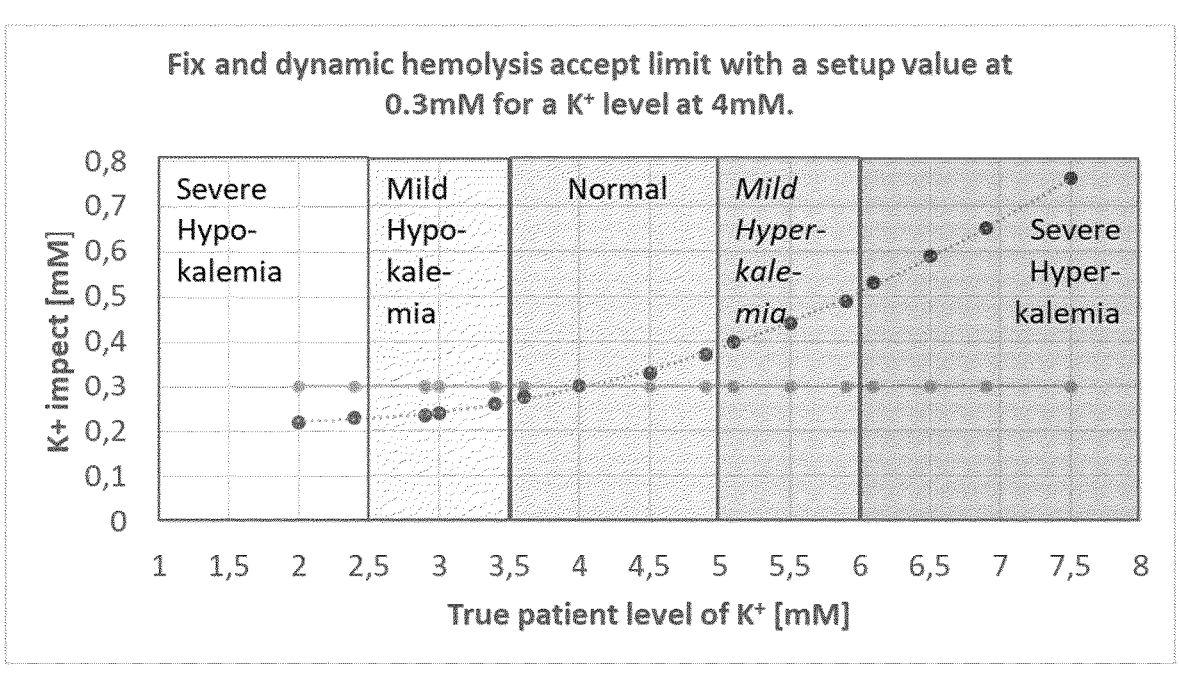
FIGS. 8-10 show fixed and non-constant cell-free hemoglobin (interference) thresholds according to, respectively, examples 1-3.

FIG. 8 furthermore shows measuring 718 concentrations, and determining 728 if the cell-free hemoglobin criticality exceeds a cell-free hemoglobin interference criticality threshold, obtaining another liquid sample comprising the analyte and cell-free hemoglobin and repeating 732 steps a-e (if the cell-free hemoglobin criticality exceeds the cell-free hemoglobin interference criticality threshold) or ending 730 the method (if the cell-free hemoglobin criticality is equal to or below the cell-free hemoglobin interference criticality threshold), such as releasing the analyte concentration to user.

In order to provide a clinically relevant apparatus and method (such as enabling assessing the clinically relevant impact of the cell-free hemoglobin on clinically relevant measured analyte concentrations), it might be relevant to obtain (quantitative) data on the interference of cell-free hemoglobin on relevant analytes. Accordingly, there is provide in TABLE I below an interference test table with an overview of interference of cell-free hemoglobin on a number of analytes, where said data is resolved with respect to cell-free hemoglobin concentration (ccfHb).

TABLE I

| | | Interference on . . . | | | | |
|---|---|---|---|---|---|---|
| Substance | ccfHb test concen- tration. mg/dL | $cK^+$ (at 4 mM) [mM] | $Na^+$ (at 140 mM) [mM] | $Ca^{2+}$ (at 1.25 mM) [mM] | $Cl^-$ (at 103 mM) [mM] | Test matrix. |
| Hemolysis | 5 | 0.0 | 0.0 | 0.00 | 0.0 | Blood |
| | 104 | 0.3 | −0.5 | −0.02 | 0.1 | Blood |
| | 159 | 0.5 | −0.7 | −0.03 | 0.4 | Blood |
| | 330 | 1.0 | −1.1 | −0.04 | −0.15 | Blood |
| | 1000 | 2.7 | −3.1 | −0.08 | −0.5 | Blood |
| | 1500 | 3.5 | −3.9 | −0.11 | N/A | Blood |
| | 2000 | 5.8 | −6.5 | −0.17 | N/A | Blood |
| | 2500 | 7.2 | −8.1 | −0.21 | N/A | Blood |
| | 3000 | 8.7 | −9.7 | −0.25 | N/A | Blood |

Furthermore, interference is quantified (via a 'correlation factor') via measurements on whole blood samples, with results being shown in TABLE II.

TABLE II

| Donor | Test levels ccfHb | Correlations factor for . . . [mM/100 mg cfHb] | | | | Number of tests | Test matrix. |
|---|---|---|---|---|---|---|---|
| | | $K^+$ | $Na^+$ | $Ca^{2+}$ | Cl– | | |
| B1906 Donor__A | 0-1000 | 0.29 | −0.32 | −0.008 | −0.05 | 50 | Blood |
| B1911 Donor__A | 0-1000 | 0.29 | −0.34 | −0.008 | −0.06 | 50 | Blood |
| B1911 Donor__B | 0-1000 | 0.27 | −0.28 | −0.007 | −0.05 | 50 | Blood |
| B1911 Donor__C | 0-1000 | 0.27 | −0.32 | −0.008 | −0.05 | 50 | Blood |
| B1911 Donor__D | 0-1000 | 0.28 | −0.32 | −0.008 | −0.03 | 50 | Blood |
| B1911 Donor__E | 0-1000 | 0.33 | −0.39 | −0.009 | −0.03 | 50 | Blood |
| B1911 Donor__F | 0-1000 | 0.31 | −0.38 | −0.01 | −0.04 | 50 | Blood |
| B2001 Donor__A | 0-1000 | 0.28 | −0.33 | −0.009 | −0.05 | 50 | Blood |
| B2001 Donor__B | 0-1000 | 0.29 | −0.32 | −0.008 | −0.07 | 50 | Blood |
| B2001 Donor__C | 0-1000 | 0.29 | −0.35 | −0.008 | −0.1 | 50 | Blood |
| Average | 1-1000 | 0.290 | −0.335 | −0.008 | −0.053 | 500 | Blood |

From TABLE II it can be derived that for potassium ions a measured analyte concentration $cA_m$, a interference from cell-free hemoglobin can be estimated as the product between the correlation factor and cell-free hemoglobin concentration, i.e., +0.3 mM/(100 mg/dL cfHb)×ccfHb (i.e., where the interference has the effect of making the measured analyte concentration higher than the true analyte concentration, so that a true analyte concentration $cA_t$ can be estimated as $cA_t = cA_m − 0.3$ mM/(100 mg/dL cfHb)×ccfHb.

In order to provide clinically relevant cell-free hemoglobin interference criticality values, e.g., with a view to being able to detect severe hypokalemia also for sample with hemolysis and/or being able to detect false hyperkalemia due to hemolysis, it might be relevant to reflect clinically relevant information, into the predetermined instructions. According to a simplified model, the clinical picture for potassium ion concentrations are as follows (for non-neonates):

$1 < K^+ \leq 2.5$ mM severe Hypokalemia $2.5 < K^+ \leq 3.5$ mM Mild Hypokalimia $3.5 < K^+ \leq 5$ mM Normal $5 < K^+ \leq 6$ mM Mild Hyperkalemia $K^+ > 6$ severe Hyperkalimia For Neonates the model is slightly different:

$1 < K^+ \leq 3.5$ mM severe Hypokalemia $3.5 < K^+ \leq 4.5$ mM Mild Hypokalimia $4.5 < K^+ \leq 6$ mM Normal $6 < K^+ \leq 7$ mM Mild Hyperkalemia $K+ > 7$ severe Hyperkalimia The above mentioned ranges embody a categorization of analyte concentrations into categories representative of certain clinical pictures, such as embodying a predetermined categorization scheme.

According to embodiments of the present invention (which in the following are explained with non-limiting reference to $K^+$, and it is for example noted that the function used can be different and the same type of model can used for, e.g., $Na^+$ and $Ca^{2+}$), the cell-free hemoglobin interference criticality may be determined by (instead of using the same cell-free hemoglobin concentration threshold at all levels of $K^+$) the threshold being arranged to be lower at low $K^+$ levels and higher for normal $K^+$ and high $K^+$ concentrations, which may result in a high quality monitoring of all $K^+$ levels together with a low number of unnecessary detection of hemolysis in the liquid sample.

It is noted that samples from the neonatal area have different reference levels (see below) but concept concepts of the present invention can be applied with the same thresholds as for adult samples.

Below are shown examples of $K^+$-concentration dependent hemolysis detection (where hemolysis detection may be considered equivalent or identical to detection of exceeding a cell-free hemoglobin inference criticality threshold) concept for 1) Clinically acceptable non-constant level vs. analytically acceptable constant level at 0.3 mM for adult samples, 2) Clinically acceptable non-constant level vs. analytically acceptable constant level at 0.5 mM for adult samples and 3) Clinically acceptable non-constant level vs. analytically acceptable constant level at 1.0 mM for neonatal samples. By 'analytical' is generally understood being rather dependent directly on concentrations without directly taking clinical considerations into account, and by 'clinically' is generally understood being rather dependent on clinical considerations.

In the examples below, reference is made to 'true patient value', which is made under an assumption of in vitro hemolysis (because in case of in vivo hemolysis, the sample concentration would also be the true patient value).

Example 1: Secure Detection of Hypokalemia (Setup Threshold: 0.3 mM)

Three different patients measured [$K^+$ concentration, $cA_m$]=2.8 mM, 5.5 mM and 6.3 mM.

Measured [ccfHb]=130 mg/dL and setup threshold: 0.3 mM (100 mg/dL).

True Patient Value, $cA_t$: Measured $K^+$–impact on $K^+$, where impact on $K^+$=130 mg/dL*0.3 mM/(100 mg/dL cfHb)=0.39 mM.

TABLE III

| A Measured [$K^+$] [mM] | B $B = 0.003*A$ Impact on [K+] [mM] | C $C = A - B$ True Patient $K^+$ [mM] | D Dynamic max impact on $K^+$: | Dynamic B ≤ D Hemolysis detected in sample. Retest/Release | Fix B ≤ 0.3 Hemolysis detected in sample. Retest/Release |
|---|---|---|---|---|---|
| 2.8 | 0.39 (12%) | 2.4 | 0.23 | Retest | Retest |
| 5.5 | 0.39(11%) | 5.1 | 0.40 | Release | Retest |
| 6.3 | 0.39(8%) | 5.9 | 0.49 | Release | Retest |

The dynamic max impact on $K^+$ is a value, which has been determined with due consideration to the underlying clinical picture(s), and which results in a cell-free hemoglobin (interference) threshold being describable as a $2^{nd}$ order polynomial function with respect to analyte concentration as depicted in FIG. 8 where the fixed threshold at 0.3 mM is also shown.

It can be seen from this example, that the non-constant threshold according to the invention is advantageous since an analyte concentration for two samples is released, whereas with a fixed sample it would have been necessary to retest (a sample for which retesting was not necessary as demonstrated with the non-constant threshold).

Example 2: Secure Detection of Hypokalemia (Setup Threshold: 0.5 mM)

Three different patients measured [$K^+$ concentration, $cA_m$]=2.9 mM, 5.0 mM and 6.4 mM.

Measured [ccfHb]=151 mg/dL and setup threshold: 0.5 mM (165 mg/dL).

True Patient Value, $cA_t$: Measured $K^+$–impact on $K^+$, where impact on $K^+$=151 mg/dL*0.3 mM/(100 mg/dL cfHb)=0.45 mM.

TABLE IV

| A Measured [K$^+$] [mM] | B = 0.003*A Impact on [K+] [mM] | C = A – B True Patient K$^+$ [mM] | D Dynamic max impact on K$^+$: | Dynamic B ≤ D Hemolysis detected in sample. Retest/Release | Fix B ≤ 0.5 Hemolysis detected in sample. Retest/Release |
|---|---|---|---|---|---|
| 2.9 | 0.45 (18%) | 2.4 | 0.33 | Retest | Release |
| 5.0 | 0.45(11%) | 4.5 | 0.57 | Release | Release |
| 6.4 | 0.45(8%) | 5.9 | 0.83 | Release | Release |

Figure 9:
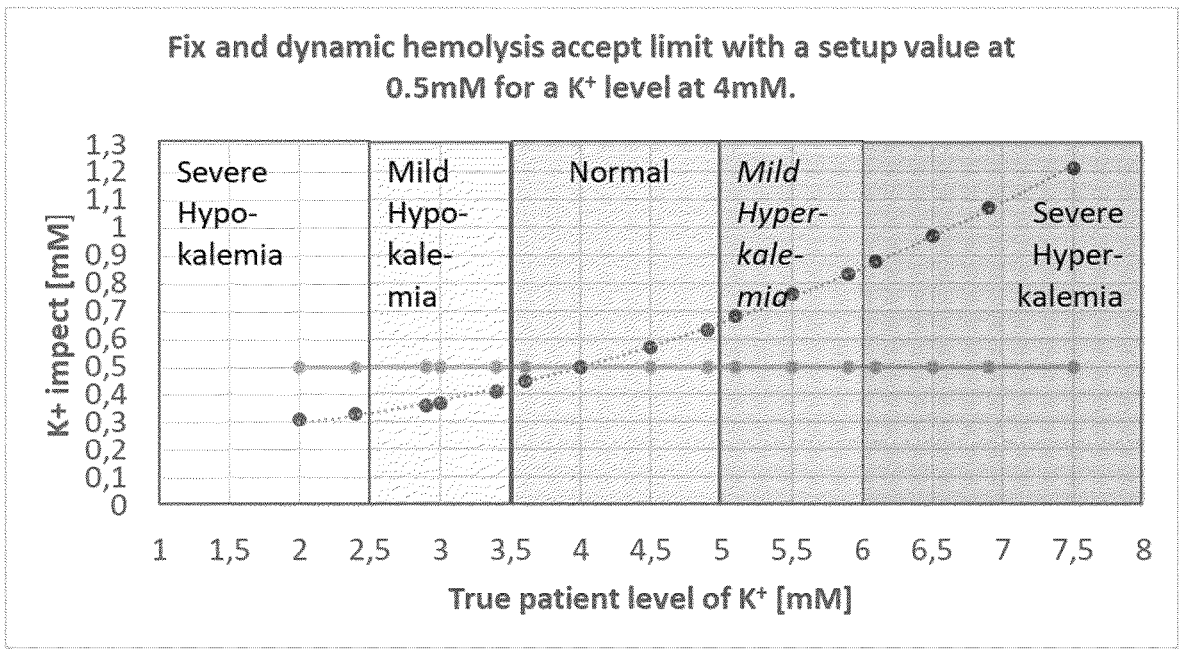

The dynamic max impact on K$^+$ is a value, which has been determined with due consideration to the underlying clinical picture(s), and which results in a cell-free hemoglobin (interference) threshold being describable as a 2$^{nd}$ order polynomial function with respect to analyte concentration as depicted in FIG. 9 where the fixed threshold at 0.5 mM is also shown.

It can be seen from this example, that the non-constant threshold according to the invention is advantageous since an analyte concentration for one sample is not released and instead a retest is requested, whereas with a fixed sample it would have been released (although retesting was necessary as demonstrated with the non-constant threshold). This could be relevant, e.g., because according to the fixed threshold, the measurement on the sample with measured K$^+$ concentration, cA$_m$=2.9 mM will be released, i.e., it could be provided to personnel whom might categorize it as indicative of mild hypokalemia. However, according to the estimated true patient K$^+$ concentration (2.4 mM) a (true patient) categorization would actually have been severe hypokalemia. However, with the (dynamic) threshold according to this embodiment of the invention, the cell-free hemoglobin interference criticality is assessed 20 to be unacceptably high and a retest is instead requested.

Example 3: Secure Detection of Hypokalemia (Setup Threshold: 1.0 mM)

Three different patients measured [K$^+$ concentration, cA$_m$]=3.8 mM, 4.5 mM and 7.0 mM.

Measured [ccfHb]=290 mg/dL and setup threshold: 1.0 mM (330 mg/dL).

True Patient Value, cA$_t$: Measured K$^+$–impact on K$^+$, where impact on K$^+$=290 mg/dL*0.3 mM/(100 mg/dL cfHb)=0.87 mM.

TABLE IV

| A Measured [K$^+$] [mM] | B = 0.003*A Impact on [K+] [mM] | C = A – B True Patient K$^+$ [mM] | D Dynamic max impact on K$^+$: | Dynamic B ≤ D Hemolysis detected in sample. Retest/Release | Fix B ≤ 1.0 Hemolysis detected in sample. Retest/Release |
|---|---|---|---|---|---|
| 3.8 | 0.87(19%) | 2.9 | 0.81 | Retest | Release |
| 4.5 | 0.87(14%) | 3.6 | 0.84 | Retest | Release |
| 7.0 | 0.87(11%) | 6.1 | 0.97 | Release | Release |

Figure 10:
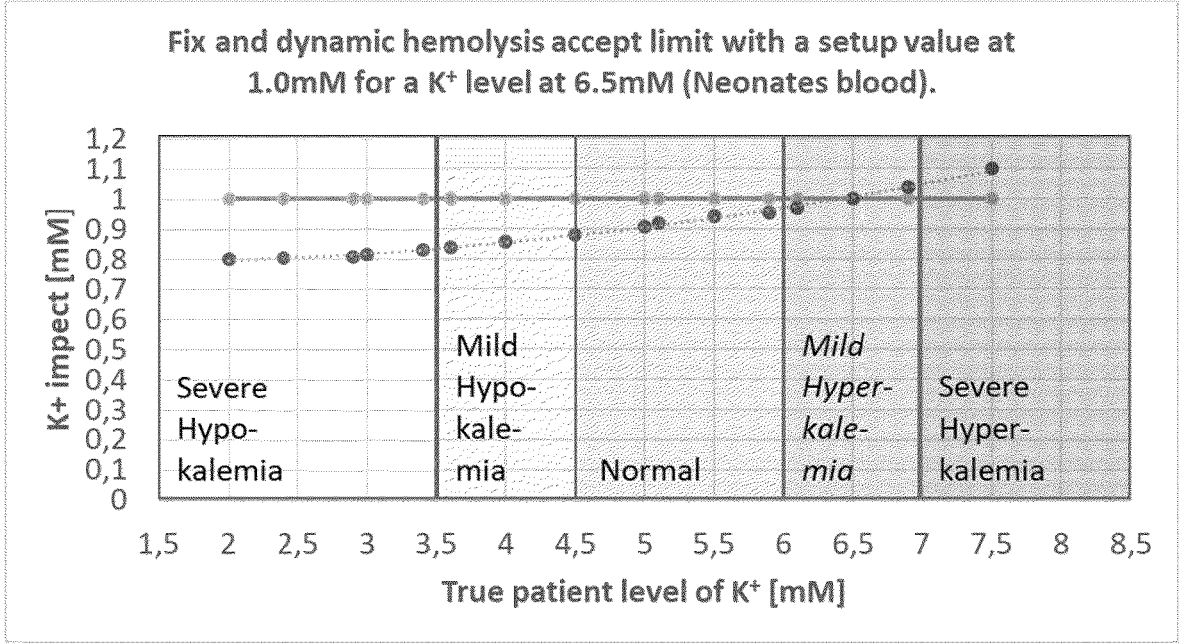

The dynamic max impact on K$^+$ is a value, which has been determined with due consideration to the underlying clinical picture(s), and which results in a cell-free hemoglobin (interference) threshold being describable as a 2$^{nd}$ order polynomial function with respect to analyte concentration as depicted in FIG. 10 where the fixed threshold at 0.5 mM is also shown.

It can be seen from this example, that the non-constant threshold according to the invention is advantageous since an analyte concentration for two samples is not released and instead a retest is requested, whereas with a fixed sample it would have been released (although retesting was necessary as demonstrated with the non-constant threshold).

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An apparatus for automatically measuring an analyte concentration in a liquid sample comprising the analyte and cell-free hemoglobin and for automatically determining a cell-free hemoglobin and for automatically determining a cell-free hemoglobin interference criticality, said apparatus comprising:

one or more sensors for measuring:

the analyte concentration in the liquid sample, and a cell-free hemoglobin concentration in the liquid sample, a data processing device comprising a processor configured to determine the cell-free hemoglobin interference criticality based on:

the cell-free hemoglobin concentration and the analyte concentration, and output a signal indicative of the cell-free hemoglobin interference criticality at least in case the cell-free hemoglobin criticality is within a predetermined range, wherein the data processing device is configured to determine the cell-free hemoglobin interference criticality by:

determining a cell-free hemoglobin interference threshold value based on the analyte concentration, determining a cell-free hemoglobin interference value based on the cell-free hemoglobin concentration, comparing:

the cell-free hemoglobin interference value, to the cell-free hemoglobin interference threshold value, and determining the cell-free hemoglobin interference criticality based on a result of the comparison, wherein the cell-free hemoglobin interference threshold based on an analyte concentration is a relative value being relative to the analyte concentration.

2. The apparatus according to claim 1, arranged for receiving the liquid sample in the form of a whole blood sample comprising red blood cells at a sample inlet and for measuring at least the cell-free hemoglobin concentration in at least a portion of the liquid sample comprising or being in liquid connection with the red blood cells.

3. The apparatus according to claim 1, and further arranged for measuring at least the analyte concentration in at least the same portion of the liquid sample for which the cell-free hemoglobin concentration was measured and/or a portion of the sample being in liquid connection with at least the portion of the liquid sample for which the cell-free hemoglobin concentration was measured.

4. The apparatus according to claim 1, arranged for measuring the analyte concentration in the liquid sample and the cell-free hemoglobin concentration in the liquid sample at spatial positions being less than 1 m.

5. The apparatus according to claim 1, arranged for receiving the liquid sample in the form of a whole blood sample comprising red blood cells at a sample inlet at a first point in time t1 and to output at a second point in time t2 the signal indicative of the cell-free hemoglobin interference criticality at least in case the cell-free hemoglobin interference criticality is within a predetermined range, and wherein a period of time between the first point in time and the second point in time is equal to or less than 10 minutes.

6. The apparatus according to claim 1, further comprising a porous element and being arranged for measuring at least the cell-free hemoglobin concentration in a portion of the liquid sample being positioned in one or more pores of porous element.

7. The apparatus according to claim 1, wherein the analyte concentration is a concentration of potassium ions.

8. The apparatus according to claim 1, wherein the cell-free hemoglobin interference threshold value based on analyte concentration is an absolute value.

9. The apparatus according to claim 1, wherein the data processing device is configured to determine the cell-free hemoglobin interference criticality by:

determining a cell-free hemoglobin concentration threshold value based on the analyte concentration, comparing the cell-free hemoglobin concentration or a parameter based on the cell-free hemoglobin concentration to the cell-free hemoglobin concentration threshold value, and determining the cell-free hemoglobin interference criticality based on a result of the comparison.

10. The apparatus according to claim 9, wherein the cell-free hemoglobin concentration threshold value based on analyte concentration is an absolute value.

11. The apparatus according to claim 9, wherein the cell-free hemoglobin concentration threshold value based on analyte concentration is a relative value being relative with respect to the analyte concentration.

12. The apparatus according to claim 9, wherein the cell-free hemoglobin threshold value is a function of the analyte concentration, and wherein the function is non-constant with respect to analyte concentration.

13. The apparatus according to claim 9, wherein the cell-free hemoglobin threshold value is a function of the analyte concentration, wherein the function is non-linear with respect to analyte concentration.

14. The apparatus according to claim 1, wherein the data processing device is operatively connected to a storage device comprising a predetermined categorization scheme, and wherein the data processing device is configured to determine the cell-free hemoglobin interference criticality by:

determining a measured category of the liquid sample based on the analyte concentration, determining an adjusted concentration, wherein the adjusted concentration is based on the analyte concentration adjusted for an interference effect of the cell-free hemoglobin, wherein the interference effect of the cell-free hemoglobin is based on the cell-free hemoglobin concentration, determining an adjusted category of the liquid sample based on the adjusted concentration, and determining the cell-free hemoglobin interference criticality based on a degree of difference between the measured category and the adjusted category.

15. The apparatus according to claim 14, wherein the cell-free hemoglobin interference criticality is either low or high, and wherein the predetermined categorization scheme is one-dimensional and comprises at least three categories, and wherein the cell-free hemoglobin interference criticality is low if the measured category and the adjusted category are identical or adjoining in the predetermined categorization scheme, and high if the measured category and the adjusted category are separated by at least one category in the predetermined categorization scheme.

16. The apparatus according to claim 1, wherein the analyte concentration is a concentration of analytes chosen from the group consisting of:

potassium ions, sodium ions, calcium ions, chlorine ions, creatinine, and lactate.

17. The apparatus according to claim 1, wherein the analyte concentration is a plurality of analyte concentrations of analytes, and wherein for at least two of the analytes:

the data processing device is configured to determine the cell-free hemoglobin interference criticality based on the cell-free hemoglobin concentration, and the analyte concentration, and output a signal indicative of the cell-free hemoglobin interference criticality at least in case the cell-free hemoglobin interference criticality is within a predetermined range, and wherein a relation between the cell-free hemoglobin interference criticality and analyte concentration is different from one analyte to another.

18. The apparatus according to claim 1, further comprising a user interface arranged for receiving user input, wherein the data processing device is configured to determine the cell-free hemoglobin interference criticality based on the user input.

19. The apparatus according to claim 1, wherein for at least one first analyte concentration, a first change in cell-free hemoglobin interference criticality changes with increasing cell-free hemoglobin concentration at a first cell-free hemoglobin concentration, and for at least one second analyte concentration, a second change in cell-free hemoglobin interference criticality changes with increasing cell-free hemoglobin concentration at a second cell-free hemoglobin concentration, wherein the first change is substantially identical or identical to the second change, the first analyte concentration is less than the second analyte concentration, and the first cell-free hemoglobin concentration is different from the second cell-free hemoglobin concentration.

20. The apparatus according to claim 1, wherein the apparatus is further arranged for measuring a concentration in the liquid sample of one or more or all of carbon dioxide, oxygen, and pH.

21. A method for automatically measuring an analyte concentration in a liquid sample comprising the analyte and cell-free hemoglobin and for automatically determining a cell-free hemoglobin interference criticality, said method comprising:

a. measuring the analyte concentration in the liquid sample, b. measuring a cell-free hemoglobin concentration in the liquid sample, c. providing to a data processing device comprising a processor, the analyte concentration and the cell-free hemoglobin concentration, d. automatically determining with the data processing device the cell-free hemoglobin interference criticality based on the cell-free hemoglobin concentration, and the analyte concentration, and e. outputting from the data processing device a signal indicative of the cell-free hemoglobin interference criticality at least in case the cell-free hemoglobin interference criticality is within a predetermined range, wherein the data processing device is configured to determine the cell-free hemoglobin interference criticality by:

determining a cell-free hemoglobin interference threshold value based on the analyte concentration, determining a cell-free hemoglobin interference value based on the cell-free hemoglobin concentration, comparing:

the cell-free hemoglobin interference value, to the cell-free hemoglobin interference threshold value, and determining the cell-free hemoglobin interference criticality based on a result of the comparison, wherein the cell-free hemoglobin interference threshold based on an analyte concentration is a relative value being relative to the analyte concentration.

22. The method according to claim 21, wherein the determination of cell-free hemoglobin interference criticality is further based on a predetermined categorization scheme, and wherein the method comprises determining the cell-free hemoglobin interference criticality by:

determining a measured category of the liquid sample based on the analyte concentration, determining an adjusted concentration, wherein the adjusted concentration is based on the analyte concentration adjusted for an interference effect of the cell-free hemoglobin, wherein the interference effect of the cell-free hemoglobin is based on the cell-free hemoglobin concentration, determining an adjusted category of the liquid sample based on the adjusted concentration, and determining the cell-free hemoglobin interference criticality based on a degree of difference between the measured category and the adjusted category.

23. The method according to claim 21, wherein the liquid sample is at least in part, such as in part or in entirety:

a sample comprising cells, a sample derived from a sample comprising cells, a whole blood sample, or a sample derived from a whole blood sample.

24. A computer program product comprising instructions which, when executed by a computer, cause the computer to receive a first information based on an analyte concentration, receive a second information based on a cell-free hemoglobin concentration, determine a cell-free hemoglobin interference criticality based on:

the cell-free hemoglobin concentration, and the analyte concentration, and output a signal indicative of the cell-free hemoglobin interference criticality at least in case the cell-free hemoglobin interference criticality is within a predetermined range, wherein the computer is configured to determine the cell-free hemoglobin interference criticality by:

determining a cell-free hemoglobin interference threshold value based on the analyte concentration, determining a cell-free hemoglobin interference value based on the cell-free hemoglobin concentration, comparing:

the cell-free hemoglobin interference value, to the cell-free hemoglobin interference threshold value, and determining the cell-free hemoglobin interference criticality based on a result of the comparison, wherein the cell-free hemoglobin interference threshold based on an analyte concentration is a relative value being relative to the analyte concentration.

* * * * *